United States Patent [19]
Munshi et al.

[11] Patent Number: 5,654,030
[45] Date of Patent: Aug. 5, 1997

[54] METHOD OF MAKING IMPLANTABLE STIMULATION ELECTRODES

[75] Inventors: M. Zafar A. Munshi, Missouri City; Chris A. Bonnerup, Houston, both of Tex.

[73] Assignee: Intermedics, Inc., Angleton, Tex.

[21] Appl. No.: 385,152

[22] Filed: Feb. 7, 1995

[51] Int. Cl.$^6$ .............................. B05D 3/06; B05D 3/10; B05D 5/12
[52] U.S. Cl. .................. 427/2.24; 427/309; 427/327; 427/534
[58] Field of Search ..................... 607/121, 129; 427/2.1, 2.24, 309, 534, 327; 204/29 OR, 291

[56] References Cited

U.S. PATENT DOCUMENTS

| | | | |
|---|---|---|---|
| 3,616,445 | 10/1971 | Bianchi et al. | 204/290 F |
| 3,853,739 | 12/1974 | Kolb et al. | 204/290 F |
| 4,189,358 | 2/1980 | Scarpellino, Jr. et al. | 204/290 F |
| 4,330,891 | 5/1982 | Branemark et al. | 3/1 |
| 4,408,604 | 10/1983 | Hirshorn et al. | 607/121 |
| 4,508,598 | 4/1985 | Giner | 204/1 T |
| 4,649,937 | 3/1987 | Dettaan et al. | 607/115 |
| 4,662,382 | 5/1987 | Sluetz et al. | 128/785 |
| 4,677,989 | 7/1987 | Robblee | 128/784 |
| 4,679,572 | 7/1987 | Baker, Jr. | 128/786 |
| 4,717,581 | 1/1988 | Roblee | 727/2 |
| 4,721,551 | 1/1988 | Byers et al. | 204/290 R |
| 4,762,136 | 8/1988 | Baker, Jr. et al. | 128/786 |
| 4,784,161 | 11/1988 | Skalsky et al. | 128/785 |
| 4,830,006 | 5/1989 | Haluska et al. | 128/419 PG |
| 4,858,623 | 8/1989 | Bradshaw et al. | 128/785 |
| 4,913,164 | 4/1990 | Greene et al. | 128/785 |
| 4,919,135 | 4/1990 | Phillips, Jr. et al. | 128/419 |
| 4,922,927 | 5/1990 | Fine et al. | 128/786 |
| 5,009,766 | 4/1991 | Lauks | 204/291 |
| 5,074,313 | 12/1991 | Dahl et al. | 128/784 |
| 5,178,957 | 1/1993 | Kolpe et al. | 428/458 |
| 5,181,526 | 1/1993 | Yamasaki | 128/784 |
| 5,203,348 | 4/1993 | Dahl et al. | 128/784 |
| 5,230,337 | 7/1993 | Dahl et al. | 607/5 |
| 5,246,014 | 9/1993 | Williams et al. | 607/122 |
| 5,267,564 | 12/1993 | Barcel et al. | 128/634 |
| 5,298,280 | 3/1994 | Kaczur et al. | 427/125 |
| 5,318,572 | 6/1994 | Heland et al. | 607/121 |
| 5,326,448 | 7/1994 | Otten | 204/402 |
| 5,330,521 | 7/1994 | Cohen | 607/122 |
| 5,330,700 | 7/1994 | Soukup et al. | 427/123 |
| 5,336,598 | 8/1994 | Hardee et al. | 204/128 |
| 5,385,579 | 1/1995 | Helland | 607/130 |
| 5,411,527 | 5/1995 | Alt | 607/122 |
| 5,411,544 | 5/1995 | Mar et al. | 607/122 |
| 5,435,896 | 7/1995 | Hardee et al. | 204/242 |

FOREIGN PATENT DOCUMENTS

| | | |
|---|---|---|
| 0388576 | 9/1993 | European Pat. Off. . |
| 2 235 666 | 1/1975 | France . |

*Primary Examiner*—Diana Dudash
*Attorney, Agent, or Firm*—C. Steven McDaniel; Conley, Rose & Tayon, P.C.

[57] ABSTRACT

The invention relates to methods of making an improved stimulation electrode for cardiac pacing and defibrillating. Specifically, the electrodes of the invention by virtue of the methods of manufacturing and using, demonstrate improved capabilities of stimulating and sensing neuromuscular tissues. The electrodes have enhanced electrically-accessible surface areas which are coated with oxides of valve and noble metals.

20 Claims, 9 Drawing Sheets

METHOD OF MAKING IMPLANTABLE STIMULATION ELECTRODES

BACKGROUND OF THE INVENTION

1. Field of the Invention

The invention relates to methods for making an improved electrode for cardiac pacing and defibrillating. Specifically, the methods of the invention produce, electrodes which demonstrate improved capabilities of stimulating and sensing electrically excitable tissues.

2. Description of the Related Art

In the human heart, a small cluster of cells called the sinus node (SN) constitutes the primary natural cardiac pacemaker. The cardiac impulse arising from the SN is transmitted to the atria on the right and left sides of the heart causing the atria to contract. The impulse from the SN is transmitted via pathways in the atria leading to another group of cells, the atrioventricular node, and then via a conduction system comprising the bundle of His, the right and left bundle branches, and the Purkinje fibers, causing the ventricles to contract. This action is repeated in a rhythmic cardiac cycle in which the atrial and ventricular chambers alternately contract and pump, then relax and fill.

The SN is spontaneously rhythmic and is termed the sinus rhythm. Secondary pacemakers in other cardiac tissues tend to be inhibited by the more rapid rate at which impulses are generated by the SN. A number of factors may affect the rate of sinus rhythm. The slower rates (below 60 bpm) are called sinus bradycardia, and the higher rates (between 101 and 160 bpm) are termed sinus tachycardia.

Disruption of the natural pacemaking and propagation system as a result of aging or disease is commonly treated by artificial cardiac pacing. Pacing is a process by which rhythmic electrical discharges are applied to the heart at a desired rate from an implanted artificial pacemaker. In its simplest form, the pacemaker consists of a pulse generator powered by a self-contained battery pack, and a lead including at least one stimulating electrode for delivery of electrical impulses to excitable myocardial tissue in the appropriate chamber(s) in the right side of the patient's heart. Typically, the pulse generator is surgically implanted in a subcutaneous pouch in the patient's chest. In operation, the electrical stimuli are delivered to the excitable cardiac tissue via an electrical circuit that includes the stimulating and reference electrodes, and the body tissue and fluids.

Pacemakers range from the simple fixed rate device that provides pacing with no sensing function, to highly complex devices that provide fully automatic dual chamber pacing and sensing functions. The demand ventricular pacemaker, so termed because it operates only on demand, has been the most widely used type, It senses the patient's natural heart rate and applies stimuli only during periods when that rate falls below the pre-set value. The dual function pacemaker is the latest in a progression toward physiclogic pacing—the mode of artificial pacing that restores cardiac function as much as possible toward natural pacing.

There has also been increasing usage of pacing in the management of tachyarrhythmias. Defibrillation ("DF"), the method employed to terminate fibrillation, involves applying one or more high energy "countershocks" to the heart in an effort to overwhelm the chaotic contractions of individual tissue sections, allow reestablishment of an organized spreading of action potential from cell to cell of the myocardium, and thus restore the synchronized contraction of the mass of tissue. The term "cardioversion" is sometimes used broadly to include DF.

Cardiac output is considerably diminished during an episode of ventricular tachycardia ("VT") because the main pumping chambers of the heart, the ventricles, are only partially filled between the rapid contractions of those chambers. Moreover, VT presents a significant risk of acceleration of the arrhythmia into ventricular fibrillation ("VF"), either spontaneously or in response to treatment of the VT. VF is characterized by rapid, chaotic electrical and mechanical activity of the excitable myocardial tissue. VF manifests an instantaneous cessation of cardiac output as the result of the ineffectual quivering of the ventricles. Unless cardiac output is restored almost immediately after the onset of VF, tissue begins to die for lack of oxygenated blood, and patient death will occur within minutes.

From the factors stated above, it is clear that the principal requirements of pacing and defibrillation, delivery of the pulse and sensing of the electrical state of the target tissue, depend heavily on the abilities of the electrodes. These functions must be routinely and unfailingly carried out over extended device implantation lifetimes. Improvements in electrodes which enhance the pulse-delivering or sensing functions or which reduce power consumption to achieve these ends are needed. It would be especially valuable to be able to achieve a more natural pacing regimen with smaller pulse generators, batteries and electrodes.

The lead assembly of a pacing electrode consists of an electrically conducting wire that is insulated from the tissue. One end of the wire connects to the pulse generator while the other end has an electrode adapted to stimulate excitable myocardial tissue on the inner surface of the heart, the endocardium (an endocardial electrode), or to the outer surface of the heart, the epicardium (an epicardial electrode). A second electrode is also connected to the body at a position through which the electrical circuit is completed in connection with body tissue and fluids. In most cases, an endocardial lead design is used for the implantable cardiac pacemaker because it can readily be inserted through a vein to introduce the stimulating electrode into the chamber to be paced. Epicardial leads require a thoracotomy to affix the stimulating electrode to the heart.

The implantable defibrillator (tachycardia pacer) essentially consists of a pulse generator powered by a combination of batteries and capacitors, and a lead assembly, In this case, the charge delivered to defibrillate the heart is several orders of magnitude larger than that from a cardiac pacemaker. However, in both cases, the stimulation depolarizes a critical mass of the heart.

Typically, electrodes for defibrillation are larger than those used for cardiac pacing because a greater area of the heart tissue needs to be stimulated. These electrodes may be in the form of patches applied directly to the heart. The most common approach in the past has been to suture two patches to the epicardial tissue via thoracotomy. It has been theorized that electrodes with large surface areas are important for a wider distribution of current flow and a more uniform voltage gradient over the ventricles. Others have postulated that uniformity of current density is important since: (i) low gradient areas contribute to the continuation or reinitiation of ventricular fibrillation, and (ii) high current areas may induce temporary damage, that then may cause sensing difficulties, set-up areas of reinitiation of fibrillation, or even potentially cause permanent damage (new arrhythmias, decreased contractility, and myocardial necrosis).

The modern trend in tachycardia pacing has been to use transvenous leads instead of thoracotomy systems. The electrodes in the lead assembly generally consist of two coil electrodes approximately 2 to 4 inches long, one placed in the right ventricle (RV) and the other in the superior vena cava (SVC) or the left brachycephalic vein. The shocking electrodes may be bipolar, in which case only one lead is used, or a combination of two leads, or one endocardial electrode and one subcutaneous patch or epicardial electrode, or two leads and a subcutaneous patch.

Factors that influence the success of defibrillation shocks include the underlying physiologic substrates of the heart, the pulse waveform of the shock, and the electrode system. In many ways, the physical criteria necessary to design bradycardia electrodes equally apply to tachycardia or defibrillation electrodes.

Two types of lead designs are in common use today, a unipolar (one wire, one electrode) and a bipolar (two wires, two electrodes) lead system. With the unipolar lead, the stimulating electrode is paced against a reference electrode remotely placed from the heart. This reference electrode is usually the metal pacemaker can. For bipolar stimulation, the reference and the stimulating electrodes are normally in close proximity to one another on the same lead and usually in the same chamber. The reference electrode in this case is a ring or sleeve electrode placed a few millimeters from the stimulating tip electrode.

In operation, the pulse generator delivers an output pulse via the lead for electrical stimulation of the excitable myocardial tissue. Stimulation is a function of the current density, i.e., current per unit area. The current required to produce a given current density decreases in direct proportion to the electrode's active or microscopic surface area.

The current from the pacemaker is also affected by a combination of the electrode impedance, the nature of the electrode-endocardial tissue/electrolyte interface, and the impedance of the pacemaker circuitry. Since modern pacemakers operate in a range between 1–2 kHz frequency, the circuit impedance becomes insignificant during pulsing when compared to that due to the electrode impedance and the electrode-endocardial tissue/electrolyte interfacial impedance (commonly termed "spreading" impedance). Hence, the electrode design and materials determine the overall current requirements of the system.

The spreading impedance of an electrode depends predominantly on the tissue resistivity affected by the overall size and shape of the electrode material, the surface characteristics of the electrode, and its reactivity with the tissue. The electrode impedance occurs within a few thousand angstroms up to a few microns from the electrode surface, and results from the charge-transfer reactions taking place at the electrode/electrolyte interface. The electrode impedance is affected by the surface area and nature of the electrode material. The impedance of the output pulse generated by the pacemaker is proportional to the macroscopic geometric surface area of the electrode and the radius of the electrode.

Stimulation requires that an electric field of adequate field strength and current density be imposed on the excitable myocardial tissue in the vicinity of the electrode to initiate rhythmic contractions. The minimum electrical pulse necessary to produce such contractions is referred to as the stimulation threshold. The greater the efficiency of the electrode to generate contractions, the smaller is the amplitude and/or duration of the pulse required to exceed the threshold. The stimulation threshold is affected by the electrode material, electrode geometry, and electrode-tissue interactions. In essence, highly efficient electrodes with low threshold voltages are desirable in order to conserve battery life. It has also been theorized that a high efficiency electrode with a lower voltage threshold and a correspondingly lower energy consumption for tissue stimulation reduces injury to tissue at the stimulation site.

At the time of implant, the acute stimulation threshold is two to three times lower than the chronic stimulation threshold observed later. The increase in threshold is attributed to a fibrous capsule which develops around the electrode tip, i.e., the development of a layer or layers of unexcitable connective tissue surrounding the electrode tip at the stimulation site. The fibrotic growth results in a virtual electrode surface area which is considerably greater than the actual surface area of the electrode. This increase in surface area lowers current densities at the tip and results in a higher stimulation threshold. The thickness of the fibrous capsule around the electrode tip is generally dependent on the fixation characteristics at the time of implant, the geometry of the electrode tip, the microstructure of the electrode tip, and the material used for the electrode. It may also be dependent on the current density at the electrode/tissue interface during the pacing pulses. A lower current density may result in less myocardial damage and hence, lead to a thinner fibrous capsule around the electrode tip. On the contrary, electrodes that have a rough surface microstructure or have sharp protrusions may be too abrasive, thereby causing irritation leading to the development of a thicker fibrous capsule.

In addition to pacing functions, the electrode must function to sense the activity of the heart by determining the aberrant behavior in the ventricular rhythms so that pacing operation will be initiated. The frequencies at which signals are typically sensed are in the bandwidth of 20–100 Hz. In these frequencies, the electrode-endocardial tissue/electrolyte interfacial impedance becomes significant. Interfacial impedance is affected by the microscopic surface area of the electrode and is established within a few microns of the electrode's surface. The microscopic surface area of the electrode is represented by all wettable surfaces including interstitial porosity, surface cracks, crevices, and channels on the surface of the stimulating electrode. Electrodes with a higher intrinsic surface area are desirable for greater sensing of the heart's activity.

Depending on the applied potential and pulse duration, activities at the electrode interface generally involve charge transfer across the electrode-tissue/electrolyte interface by a combination of faradaic processes or oxidation-reduction reactions and double layer charging. As current densities increase, these reactions change the ionic concentration at the interface, requiring migration of ions from increasingly greater distances. The greater the current density, the larger are the polarization losses on the electrode. The concentration gradient set-up at the electrode/electrolyte interface is the source of the after potential.

Current density is related to the pacing threshold and sensing capability (amplitude of the depolarization events), i.e., if the current density is too high, the electrode is perturbed more from its initial equilibrium voltage thereby decreasing its sensing capabilities. If the current density is low, the voltage of the electrode is less perturbed and therefore sensing is less affected. Sensing is at its most optimum at a lower current density. However, a finite current density is required for cardiac muscle depolarization. Certain improvements in sensing have been achieved (see; e.g., U.S. Pat. No. 5,267,564 which relates to a pacemaker lead for sensing a physiological parameter of the body, a portion of which lead comprises a platinum-iridium outer cap).

In all types of stimulation electrodes, the electrode itself must be both chemically corrosion resistant and mechanically stable enough to withstand chronic application. It must possess a high charge capacity. It must also inject a substantial level of electric charge into the tissue to be stimulated. Finally, the ability to inject charge must not deteriorate significantly over time after implantation.

Stimulation of tissues requires that the charge be injected reversibly by a purely capacitive mechanism. In such a mechanism, the electrode behaves as a charge flow transducer between media exhibiting different charge flow properties. The capacitive mechanism allows electrons to flow away from the stimulation electrode causing electrical charges at the electrode/electrolyte interface to orient themselves in order to cause a displacement current through the electrolyte. Since the electrolyte is an ionic medium, the slight displacement of the ions in reorientation creates a charge flow.

When irreversible chemical reactions begin to occur, the mechanism is no longer capacitative. Irreversible faradaic reactions may lead to water electrolysis, oxidation of soluble species, and metal dissolution. In addition, some of the products of the reactions may be toxic. Neither gas evolution nor oxide formation reactions contribute to electrical stimulation of excitable tissue. The stimulation energy is wasted in electrolyzing the aqueous phase of blood instead of carrying desirable charged species from one electrode to the other via the tissues. Stimulation electrodes should preferably allow a large charge flow across the electrode-tissue interface without the risk of irreversible faradaic reactions. Selection of the metal of the electrode is critical.

A metal of choice in electrode manufacturing has traditionally been titanium. On a fresh titanium surface, however, oxygen ions react with the titanium anode to form an oxide layer. Once a finite oxide thickness has been formed on the surface, polarization increases further. A point is reached when the oxygen ions reaching the surface of the titanium cannot be reduced further to form the oxide, and instead are reduced to elemental oxygen to form oxygen gas. The oxide film developed on the surface of a titanium electrode, either naturally or electrochemically, is irreversible. It cannot be reduced to the original metal by passing a charge in the reverse direction. Hence, it is clear that virgin titanium metal is a poor choice for electrode construction since it forms a semi-conductive oxide on its surface before and even during the electrical stimulation. Platinum, and much more so stainless steel, have been shown to undergo irreversible dissolution during stimulation as well.

Titanium oxidation reactions are several times more likely in an oxidative environment than those of platinum or platinum alloys, but a thousand times less so than those of stainless steel. Unfortunately, due to the expense of platinum metal and the requirement for large amounts of metal in patch-type electrodes, production costs are too high for platinum electrodes. Therefore, even though oxidation problems are more prevalent in them, titanium electrodes are typically used.

From the equation $C=k\epsilon A/d$: where $\epsilon$ is the permittivity of vacuum, A is the real surface area of the film, k is the dielectric constant of the film, and d is the thickness of the porous material, it can be seen that in order to achieve a large charge-storage capacity, the porosity of the dielectric may be maximized with a large accessible surface area. Numerous types of cardiac pacing and defibrillation electrodes have heretofore been developed with these and other factors in mind, utilizing various configurations and materials asserted to promote lower stimulation thresholds and improved electrical efficiencies. Thus, for both bradycardia and tachycardia applications, it is desirable to minimize the electrical impedance at the electrode-tissue interface by increasing the intrinsic surface area of the electrode or by reducing formation of a capsule of inactive tissue that surrounds and isolates the electrode from active tissue.

Microporous electrodes based on sintered titanium, sintered titanium nitride, and microporous carbon or graphite have been used with some degree of success. However, the electrode reactions in aqueous solutions involve significant gas generation similar to the behavior of native titanium. Sanding or sandblasting electrode surfaces is a broadly used method to achieve surface area enhancement. For example, French Patent 2,235,666 relates to a stainless steel electrode tip which is sanded to increase surface area and reduce the impedance of the electrode.

Other methods have also been used. U.S. Pat. No. 5,318,572 relates to a platinum-iridium (90:10) porous electrode with recess slots in the shape of a cross and at least one, preferably two variably-sized, porous coating/s of 20–80 micron diameter platinum-iridium (90:10) spheres deposited on the surface of the electrode. On top of this structure, a reactively sputtered coating of titanium nitride is applied. U.S. Pat. No. 4,156,429 describes a means for increasing the reactive surface area by forming a highly porous sintered electrode body consisting of a bundle of fibers, preferably of platinum but alternatively of Elgiloy, titanium, or a platinum-iridium alloy. Conversely, the fibers may be encompassed within a metallic mesh to yield a seventy percent to ninety-seven percent porosity. U.S. Pat. No. 5,203,348 relates to defibrillation electrodes which can be formed on titanium ribbons or wires with a sputtered outer layer of platinum, or a silver core in a stainless steel tube with a platinum layer formed onto the tube. A divisional of that patent (U.S. Pat. No. 5,230,337) discloses that the coating is preferably made by sputtering to apply a "microtexture" to increase the surface area of the electrode.

U.S. Pat. No. 5,178,957 relates to electrodes and a method of making electrodes including pretreatment of the surface by sputter-etching and sputter-depositing a noble metal on the surface. U.S. Pat. No. 5,074,313 relates to a porous electrode with an enhanced reactive surface wherein surface irregularities are introduced to increase surface area by glow discharge or vapor deposition upon sintered wires. U.S. Pat. No. 4,542,752 describes a platinum or titanium substrate coated with a porous sintered titanium alloy which in turn is coated with a porous carbon. The latter was claimed to promote tissue ingrowth and provide low polarization impedance. U.S. Pat. No. 4,784,161 relates to making a porous pacemaker electrode tip using a porous substrate, where the porous substrate is preferably a non-conductive material such as a ceramic or a polymer made porous by laser drilling, sintering, foaming, etc. to result in pores 5–300 microns in depth. U.S. Pat. No. 4,603,704 features a hemispherical electrode made of platinum or titanium, coated with a porous layer consisting of a carbide, nitride, or a carbonitride of at least one of the following metals; titanium, zirconium, hafnium, molybdenum, niobium, vanadium, or tungsten. U.S. Pat. No. 4,281,668 discloses a vitreous carbon or pyrolytic carbon electrode that is superficially activated, e.g., by oxidation, for microporosity. The electrode is then coated with a biocompatible ion-conducting, hydrophobic plastic. The latter is said to substantially prevent thrombus formation.

Despite the numerous means of increasing the surface area to reduce polarization losses and after potentials and the use of noble metals and their alloys as electrodes as described above, with varying degrees of success, there remain significant problems pertaining to polarization losses and sensing difficulties. In order to make further improvements to the electrode, stable oxides of some of these noble metals have been employed as a coating, It is known that certain metals, metallic oxides, and alloys are stable during electrolysis, and that these metals are useful in a variety of electrode applications such as chlor-alkali electrolysis (see, e.g., U.S. Pat. No. 5,298,280). Such metals typically include the members of the platinum group; namely, ruthenium, rhodium, palladium, osmium, iridium, and platinum. These metals are not suitable for construction of the entire electrode since their cost is prohibitive. Therefore, these metals or their alloys, or as metallic oxides, have been applied as a thin layer over a strength or support member such as a base member made of one of the valve metals (Ti, Ta, Nb, Hf, Zr, and W). These valve metals or film-forming metals as they are sometimes known, are much less expensive than platinum group metals and they have properties which render them corrosion resistant. However, as previously mentioned, they lack in good surface electro-conductivity because of their tendency to form on their surface an oxide having poor electroconductivity.

As noted previously, titanium is generally the metal substrate of choice since it is lightweight and relatively inexpensive compared to the other metallic substrates. However, Ti has a naturally occurring oxide passivated on its surface having a rutile structure. This oxide is fairly non-conductive and has to be removed before titanium can fully function as an electrically conductive substrate. Various procedures have been employed in prior art to "etch" this film away. For instance, U.S. Pat. No. 5,181,526 relates to an electrode comprising platinum or titanium and a mixture of platinum and a platinum group metal oxide coated thereon, where an upper portion of the electrode is a mesh or is porous, and the electrode head is electrolytically corroded to remove the oxide using NaCl-HCl or hot oxalic acid solution prior to deposition of the platinum-iridium coating.

It is known that titanium oxide and the oxides of the other valve metals have better semi-conducting properties than the native oxide when doped with other elements or compounds which disturb the lattice structure and change the conductivity of the surface oxide. Metal oxides other than titanium oxide when intimately mixed and heated together have the property of forming semiconductors, particularly mixed oxides of metals belonging to adjacent groups in the Periodic Table. It is also known that platinum group metals and platinum group metal oxides may be coated on the surface of the valve metals to achieve this semi-conducting properties. U.S. Pat. No. 4,717,581 teaches the use of iridium oxide coated electrodes for neural stimulation. A metallic electrode made of platinum, platinum-iridium alloy, stainless steel, stainless steel alloys, titanium, titanium alloys, tantalum, and tantalum alloys is coated with iridium oxide to form the electrode. U.S. Pat. No. 4,679,572 discloses an electrode with a conductive tip portion and a substrate composed of a material conventionally employed for pacing electrodes, and a layer of film of iridium oxide overlying the surface of the substrate. The tip portion may be provided with recesses to which the iridium oxide surface layer is confined.

Valve metals have the capacity to conduct current in the anodic direction and to resist the passage of current in the cathodic direction, (i.e., the anodic reaction is irreversible) and are sufficiently resistant to the electrolyte media. In the anodic direction, however, their resistance to the passage of current goes up rapidly, due to the formation of an oxide layer thereon, so that it is no longer possible to conduct current to the electrolyte in any substantial amount without substantial increases in voltage which makes continued use of uncoated valve metal anodes in the electrolytic process uneconomical and inefficient.

In order to avoid this passivation on the surface of the valve metal, a metal oxide or a mixed metal oxide of the platinum group is used. The oxide from this group is very stable and does not grow further. In addition, it provides a protection for the underlying metal. Many of these oxides are generally reversible to aqueous based redox species and hence undergo reversible redox reactions with species such as hydrogen ions and hydroxyl ions leading to the formation of higher oxidation state surface oxides.

Electrodes capable of more natural pacing and defibrillation are needed. Improved electrodes should have the following features for efficient stimulation of the myocardial tissue: smaller geometric macroscopic surface area and smaller electrode radius; higher intrinsic microscopic surface area; and appropriate surface nature, for achieving: (1) finite low current drain; (2) finite current density; (3) high pacing impedance; (4) low sensing impedance; (5) greater efficiency to produce contractions of the heart wall at lower voltage threshold; and (6) lower tissue irritations and hence lesser fibrotic growth.

SUMMARY OF THE INVENTION

Methods of making improved electrodes which overcome at least certain of the disadvantages of the prior art method for making such electrodes are provided by the present invention. By the practice of the methods, electrode design improvements are provided which enhance the reduction in polarization voltage while substantially enhancing the ability of the implantable electrode to sense cardiac activity. The electrodes made by the methods of the invention do not cause as much inflammation or irritation of adjacent tissues as prior art electrodes and thereby avoid elevating pacing thresholds. Substantially improved porous surfaces are provided on the lead electrodes which allow smaller surface areas to be used.

This invention relates, in part, to methods of making new electrodes for chronic electrical stimulation of living tissues such as the nervous system, muscles, and the likes used in combination with an electrically driven implantable device. New electrode designs for cardiac pacing, defibrillation, or other electrical stimulation of tissues having a much improved surface will provide a more uniform distribution of current and stimulate the tissue at a much lower voltage threshold. One embodiment of the invention includes electrodes with a higher effective geometric surface area that provides the ability for stimulation, such as cardiac pacing at a much lower voltage threshold. Another embodiment involves the selective chemical etching and coating with a corrosion-resistant stable oxide which will significantly reduce polarization losses (that would otherwise result in gas evolution) and increase the ionic energy transfer reactions between the two electrodes such as those used in defibrillation. The coating enhances the uniformity of the current distributed across the electrode surface allowing a higher confidence level that successful defibrillation will occur at lower threshold voltages. The new designs will facilitate in conserving battery power and also allow for the further miniaturization of the electrode with optimum quality control.

The improvements of the present invention rely in part on removing surface oxide via a suitable process followed by protection of the titanium surface through a suitable corrosion resistant coating significantly reducing the polarization losses and improving the efficiency of the energy transfer through the tissue between the two stimulation electrodes.

Generally, improved methods for making and using improved implantable stimulation electrodes are disclosed. The electrode comprises in the first instance, a metal surface. Such surfaces may be any suitable metal surface for use as an electrode as large as approximately 50 cm$^2$ to as small as approximately 0.01 cm$^2$. The metal surface is a surface which is capable of being substantially exposed to a target tissue such as the cardiac muscle by implantation in or near the target tissue. The surface may be a planar surface such as the planar surface of patch-type electrodes. The surface may also be one which is curved such as the helical surface of loosely coiled wire (in diameters of from approximately 0.1 to 1.0 mm) defibrillating electrode leads. The surface may also be one which is tubular or cylindrical in shape with an overall length of approximately 10 to 100 mm, an outer diameter of approximately 1–7 mm, and an inner diameter of approximately 0.9 to 1.2 mm. The surface may also be spherical or hemispherical with radii of approximately 0.1 to 2.0 mm.

The surface is also a surface substantially devoid of native metal oxides. A native metal oxide is defined for purposes of the invention as a metal oxide derived from oxidation of the molecules of the metal actually comprising the metal surface. Such a native metal oxide is also defined for purposes of this invention as being other than a non-native metal oxide. A non-native metal oxide is defined for purposes of this invention as a metal oxide derived by oxidation of a metal other than the molecules of the metal actually comprising the metal surface of the electrode. In most instances, the non-native metal oxide will also be the oxide of a metal molecule which is itself different from the molecules of the metal actually comprising the metal surface of the electrode.

Thus, if the metal comprising the metal surface is titanium, a native metal oxide would be derived by exposure of the titanium metal surface to an oxidative environment to form on the surface titanium oxide by combination of molecules of the titanium actually comprising the metal surface with oxygen. Conversely, using techniques known to those of skill in the art of electrode manufacturing, it is possible to expose a metal surface comprising titanium which is substantially devoid of any native titanium oxide to a chemical solution which solution causes to be formed on the titanium metal surface a coating or layer of a metal oxide comprising metal molecules other than those actually comprising the metal surface. Such a metal oxide would be non-native even if the metal comprising the metal surface of the electrode were of an identical chemical nature with the metal molecules which combine with oxygen to form the non-native metal oxide which is then coated or layered upon the metal surface. Thus, it is possible using the definitions and methods of the invention, for instance, to produce a non-native titanium oxide and layer the non-native titanium oxide upon a titanium metal surface which is substantially devoid of native titanium oxide. It is also possible using the definitions and methods of the invention, for instance, to produce a non-native metal oxide of a metal other than titanium, iridium for example, and layer the non-native metal oxide (iridium oxide for example) upon a titanium metal surface which surface is substantially devoid of native titanium oxide.

The surface of the electrode is essentially devoid of all native metal oxide. Most preferably, the electrical impedance of the electrode will not be increased by any amount due to the presence of native metal oxides. Typically, a variety of methods are used to exclude native metal oxides from the metal surface to create a surface substantially devoid of native metal oxide. These methods may be mechanical (for example, sandblasting) or they may be chemical (for example, acid washing). However, as will be further described below, it is important for purposes of the invention to distinguish between such methods which are used merely to remove the native metal oxides from the surface.

The metal surface is also a surface further comprising a metal selected from the group of metals consisting of valve metals or their alloys. Valve metals are known to those of skill in the art of metallurgy and comprise metals such as Ti, Ta, Nb, Hf, Zr, and W. In certain preferred embodiments Ti will be the metal of choice for the metal surface.

The metal surface of the electrode further comprises an electrically-accessible area. The electrically-accessible area of the metal surface is that portion of the metal surface which is capable of causing a suitable electrical current to pass from the electrode to the target tissue in order to appropriately stimulate the target tissue. Thus, the electrically-accessible area is that portion of the metal surface of the electrode capable of causing an electrical pulse to pass from the electrode to the target heart tissue in order to effectively cause the heart muscles to contract. It is estimated that such efficiency is on the order of about 90–99% for bradycardia electrodes of the invention and on the order of about 90–98% for tachycardia electrodes of the invention (i.e., the ratio of energy delivered by the electrode divided by the energy delivered by the stimulation system to the electrode, where losses are most likely due to joule-heating of surrounding tissues). It is the electrically-accessible area of the metal surface of the electrodes of the invention which is maximized by both the macroscopic and microscopic enhancement techniques of the invention prior to deposition of the metal oxide coat or layer, which deposition itself is a form of surface area enhancement.

The electrically-accessible area of the metal surface of the electrode further comprises a macroscopically-enhanced surface area. For purposes of the invention, macroscopically-enhanced surface area is that portion of the electrically-accessible area of the metal surface of the electrode which has been grossly modified in a manner which causes greater electrically-accessible area to occur per unit area across the metal surface. Thus, if a patch-style electrode to be constructed by the methods of the invention is a square metal surface 10 mm×10 mm comprising a unit area across the metal surface of 100 mm$^2$ all of which is electrically-accessible as defined by the present disclosure, then without modification of the gross (macroscopic) configuration of that metal surface, the electrically-accessible area will also be 100 mm$^2$. After macroscopic-modification, while the unit area across the metal surface has not increased and still occupies a 10 mm×10 mm square, the electrically-accessible area will be greater than 100 mm$^2$ due to the macroscopic modifications such as indentation and corrugation.

The macroscopically-enhanced area of the electrode may be an area which is indented. The term "indent" or its derivatives, for purposes of the invention, means the production of cup-shaped, tube-shaped, or cylinder-shaped receptacles in the metal surface. Such indentations are those made so that the mouth of the cup or tube is coplanar with the metal surface, while the fillable portion of the cup or tube protrudes inwardly from the metal surface. The term "corrugate" or its derivatives, for purposes of the invention, means bending of the metal surface in and out of the plane of the original metal surface. Other types of macroscopic enhancement may be used including machining into the electrode surface large holes or channels (including crossed and intersecting), waffle-surfacing, and the like, known to those of skill in the art.

As will be described in detail hereafter, such indentations or corrugations are made using milling or molding techniques known well to skilled metal workers conversant with building implantable electrodes. Thus, as is typically done in the art of building defibrillating electrical leads, an originally straight wire is coiled in order to macroscopically-enhance the electrically-accessible area per unit area of the metal surface. Of course, other means of macroscopically-modifying the metal surface such as addition of layers of metal mesh, wire or spheroids, as well as sintering or sputtering metal particles into the surface, may be used in a manner consistent with the present invention and are included within the meaning of macroscopic modification. Additionally, it is of course possible to macroscopically modify the metal surface using combinations of two or more such techniques. Thus, for example, an originally flat metal surface of a patch electrode to be produced by the methods of the invention, may be first drilled or molded in order to produce indentations in the metal surface. The indented surface may thereafter be bent to introduce corrugations to the surface. Whichever technique or combination of techniques is selected according to the invention, the result of making such modifications to the metal surface is to cause the electrically-accessible portion of the metal surface to be macroscopically-enhanced.

Where indentation is utilized to introduce a multiplicity of tube-shaped receptacles in the metal surface, these receptacles are between about 10 and 90% of the depth of the metal surface, where the metal surface is to be used on only a single side (where double-sided, 1–49% depths are preferred), and are between about 20 and 100 micrometers in diameter. Additionally, the receptacles occur at a density maximum dictated by the radius of the receptacle (receptacles no closer than the radius length of the average receptacle). Certain preferred densities of receptacles occur at a density of at least approximately 350 receptacles per square millimeter of said metal surface. Corrugation of the metal surface of an electrode of the invention will achieve macroscopic-enhancement by creating a valley-to-peak distance of approximately 1.0 mm and a density of peaks or valleys of approximately between 1.05/mm. Where corrugation is used to enhance the electrically-accessible area, it does so by a factor of at least 85% or 1.85 times that observed in the uncorrugated surface.

After the metal surface of the electrode has been macroscopically-enhanced as to area, further enhancement is achieved by microscopically-enhancing the surface area. For purposes of the invention, microscopically-enhanced surface area is that portion of the electrically-accessible area of the metal surface of the electrode which has been finely modified in a manner which causes greater electrically-accessible area to occur per unit area across the metal surface. Thus, extending the example of the patch-style electrode where the metal surface is 100 mm$^2$ and entirely electrically-accessible, and the surface is modified macroscopically to increase the electrically-accessible area to greater than 100 mm$^2$, say two-fold up to 200 mm$^2$, then microscopic enhancement will increase the electrically accessible area over and above that achieved by macroscopic enhancement, say an additional two-fold up to 400 mm$^2$.

The microscopically-enhanced area of the electrode may be an area which is involuted by controlled chemical corrosion or ion bombardment. For purposes of the invention, "involute" and its derivatives means removal of molecules of the metal comprising the metal surface in order to pit the surface. The inventors have discovered that typical means of involuting a metal surface such as sandblasting have limited usefulness, In particular, if steps are taken to macroscopically-enhance a metal surface, techniques such as sandblasting are counter effective in that much of the enhanced surface area may be inaccessible to the sand particles used in abrasion. For instance, as with the use of indentations as disclosed in the present invention, sandblasting would not appropriately abrade the enhanced surface areas because the particles would not reach the interior of the indentations. Additionally, sandblasting a surface macroscopically-enhanced with indentations as described will destroy or at least partially block many if not most of the mouth regions of the tube-like indentations.

Therefore, the methods of the invention preferably use means other than surface abrasion by sandblasting and the like. One such method involves the use of controlled chemical corrosion by exposure to an acid. As used herein, "controlled corrosion" or its derivatives, refers to treatment with a corrosive composition which by its nature has access to all surfaces of the macroscopically-enhanced surface.

As noted above, it is critical to the understanding of the present invention to distinguish the many uses of acids in metal surface treatment, from the controlled chemical corrosion taught herein. In many instances, certain of these disparate techniques are lumped under the general terms "acid etching" or "acid corroding" or "acid washing," while leaving the underlying metal molecules of the actual, integrated metal surface substantially intact.

For instance, it is known in implantable electrode arts to treat a metal surface of an electrode with an acid in order to remove ions and other products of milling processes from such surfaces, and in order to improve surface adhesion of subsequently applied coatings. U.S. Pat. Nos. 4,717,501, 4,677,984 and 5,181,526 teach uses of such acid treatments in order to remove surface debris and ions from electrode surfaces prior to subsequent manufacturing methods. These treatments utilize HCl, and are not capable of efficiently removing native metal oxides from the electrode surfaces. Additionally, it is known to remove at least a portion of the native metal oxidation from such metal surfaces to increase the reduction-oxidation capabilities of the electrode (see, e.g., U.S. Pat. No. 5,298,280). It is also known to use acid solutions in order to layer or coat metal oxides onto the metal surface of an electrode. U.S. Pat. Nos. 4,717,581 and 4,677,989, for instance, teaches the formation of and acid/alcohol solution containing dissolved iridium chloride complexes for use in deposition of iridium oxide onto the metal surface of an electrode (see also, e.g., U.S. Pat. No. 4,762,136).

While certain of the above uses of acids in treatments of a metal surface of an implantable electrode are useful as secondary methods in the manufacturing of the electrodes of this invention, the aforementioned uses of acids are not designed to corrode the metal surface of the electrode in a uniform and controlled manner in order to microscopically enhance the area of the metal surface. To the contrary, after macroscopic enhancement is accomplished, the methods and devices of the invention chiefly utilize contact of the metal surfaces of the electrode with an acid in order to remove molecules of the metal comprising the metal surface leaving a uniformly pitted surface of metal. As will become evident in the detailed descriptions and figures to follow, the use of the acid as intended to enhance the surface area which is electrically-accessible, results in a microscopically-enhanced surface markedly greater and more uniform in nature than those previously known in the implantable electrode arts.

A principal advantage recognized by the inventors with the use of an acid in this manner is that a macroscopically-enhanced surface as disclosed herein may be thereafter effectively treated along all of its surfaces without causing closure or other surface-reducing effects on the macroscopically-enhanced surface. In particular, where very narrow tube-like indentations are utilized to macroscopically-enhance the metal surface area of the electrode, acid solutions used to microscopically enhance the surface area fully penetrate such receptacles to reach all surfaces therein.

As opposed to this advantageous characteristic of controlled chemical corrosion, sandblasting as is typically used to treat an electrode surface results in a highly non-uniform surface. Due to its abrasive characteristics, sandblasting would fail to provide the degree of enhancement necessary. Moreover, sandblasting and like techniques as practiced previously in the implantable electrode arts is as likely to decrease a macroscopically-enhanced surface by closing or otherwise eliminating at least certain of the newly exposed surfaces.

The acids used to microscopically-enhance the metal surfaces are those acids known to those of skill in the arts of metallurgy to corrode metal surfaces. Thus, acids such as: 10–20% HCl at 50°–100° C., preferably 10% HCl at 65° C.; 10–75% $H_2SO_4$ at 25°–50° C., preferably 65% $H_2SO_4$ at 38° C.; 5–10% $H_3PO_4$ at 50°–100° C., preferably 25% $AlCl_3$ at 100° C.; 5–70% $CaCl_2$ at 100°–175° C., preferably 70% $CaCl_2$ at 175° C.; and 10–90% formic acid at 100° C. to boiling point, preferably 50% formic acid at the boiling point. Even more preferably, the acid used in a controlled corrosion of the metal surface of the electrode to microscopically-enhance the surface is oxalic acid. More particularly, oxalic acid is used where 1–25% oxalic acid is contacted with the surface at 50°–100° C. Preferably, such treatment will be made using 10% oxalic acid at 80° C.

The microscopic-enhancement techniques of the present invention are those that create a uniformly pitted surface on the metal with pits occurring at a density of at least approximately 50,000 pits per square millimeter of surface area. More preferably, such pits occur at a density of at least approximately 75,000 pits per square millimeter of surface area. Even more preferably, such pits occur at a density of at least approximately 110,000 pits per square millimeter of surface area. Additionally, such pits are approximately 3 µm to 10 µm in diameter, and are approximately 5 µm to 10 µm in depth. More preferably, such pits are approximately 5 µm to 9 µm in diameter, and are approximately 6 µm to 8 µm in depth. Even more preferably, such pits are approximately 8 µm in diameter, and are approximately 8 µm in depth.

Where the implantable stimulation electrode of the invention is microscopically-enhanced over its surface area by controlled chemical corrosion, such treatments enhance the electrically-accessible area over that provided by macroscopic enhancement by a factor of at least 22-fold, more preferably by a factor of 27-fold, and even more preferably by a factor of 32-fold. Where the implantable stimulation electrode of the invention is microscopically-enhanced over its surface area by controlled ion bombardment, such treatments enhance the electrically-accessible area over that provided by macroscopic enhancement by similar-fold factors.

A final form of surface area enhancement is provided by the invention by applying coatings of metal oxides. Such enhancement occurs by virtue of the preferred fit which is possible using mixed-sized metal oxide molecules in lattice arrangements. Thus, whereas a single metal oxide produces a mono-lattice with routine gaps where molecules abut one another, a mixed metal oxide with differently sized molecules produces a binary lattice where the gaps of the mono-lattice may be filled by the smaller of the two molecules. Similarly, where a binary lattice may have gaps between the contact points of the two molecules making it up, if a third differently sized metal oxide is added, further gap-filling is possible. Such arrangements provide a means of substantially enhancing the surface area of the underlying electrode, especially if used in combination with the macro- and micro-enhancements techniques of the present invention.

A non-native coating is also applied upon the metal surface comprising a metal oxide or a mixture of at least two metal oxides selected from the group of metal oxides consisting of oxides of valve metals capable of reversible reduction-oxidation. This accomplishes not only surface enhancement but also protects against recurrence of the native oxide thereby enhancing performance of the electrode. As described above, such a coating is prepared by oxidizing metal molecules other than the metal molecules comprising the metal surface. A variety of techniques can be utilized to layer or coat the non-native metal oxide onto the metal surface, some of which will be described in more detail below. However, in each such instance, the method used to apply the coating is one in which an even and complete coating is made over the entire electrically-accessible area including each area which has been enhanced by macroscopic or microscopic treatment of the metal surface. In particular, the method of applying the coating is one which does not substantially subtract from the enhancements of the electrically accessible area. For example, in the case of a macroenhanced metal surface comprising tube-like indentations, the layer process does not block access to the receptacle by layering over the mouth of the tube-like indentation. Similarly by way of example, where a microscopically enhanced surface comprises a metal surface pitted by controlled chemical corrosion, the layering process does not substantially block access to the pits therein. Thus, while layers are applied of non-native metal oxides, such layering is designed to fully take advantage of the enhancements of the surface area achieved through the prior treatments.

The non-native metal oxides of the invention consist of oxides of valve and/or platinum group metals capable of reversible reduction-oxidation. In certain preferred electrodes, the mixture comprises a mixture of ruthenium oxide, iridium oxide, and tantalum oxide. In even a more preferred electrode, the coating of metal oxides will be a three-part composition of ruthenium oxide, iridium oxide, and tantalum oxide in a ratio of 50:25:25 weight percent, respectively.

In a surprising finding using the electrodes of the invention, it was found that the electrodes are capable of reducing the amount of both acute and chronic coagulation of blood surrounding the electrode. It is postulated that this reduction in the amount of coagulation of blood is a direct result of the reversible reduction-oxidation occurring over the enhanced electrically-accessible area of the electrodes. Where coagulation occurs immediately upon placement of the electrode in the tissue, it is said to be acute. Certain prior art electrodes have failed to be essentially reversible in redox reaction along their surfaces where the build up of the irreversible electrochemical products upon the surface results in entrapment of ions, molecules, etc. derived from the serum or tissue in closest contact with the electrode surface (chronic coagulation, fibrotic growth). This in turn results in a greater likelihood of coagulation of blood, fibrin formation and other clotting cascade moieties immediately next to the surface or entrapped therein. These entrapped and surface blocking particles further reduce the ability of the surface to pass a charge and lead to increased impedance across the electrode surface.

The electrodes of the invention, on the contrary, undergo essentially freely and completely reversible reduction-oxidation across the surface of the electrode. Thus, there is a continual sloughing of any particles that temporarily may become entrapped by redox products on the surface. Since this renewal process is reinitiated upon each pulse or charge delivery, there is a much greater active surface life for the electrodes of the invention over those previously known.

It is particularly important that such sloughing and renewal take place for the electrodes of the invention over those of the prior art. This is because the electrodes of the invention rely upon both macro- and micro-enhancement of the surface of the electrode to greatly increase the electrically-accessible surface area of the electrodes. Especially in the case of the use of tube-like indentations and of the micro-pits of the metal surface as provided herein, non-reversible reduction oxidations and the attendant build up of sera particles across such surfaces would lose at least a portion of that gained by surface area enhancement.

Because of their enhanced area and their ability to constantly renew their electrically-accessible surfaces, the implantable stimulation electrodes of the invention are capable of surprisingly enhanced sensing of the electrical state of the excitable tissue most closely adjacent to the electrode, both acutely (immediately after implantation) and chronically (substantially after implantation). The sensing of the electrical state of the target tissue occurs between the pulses and is achieved via the metal surface. Therefore, those treatments and improvements which enhance the ability of the electrode to deliver a pulse, also enhance its ability to sense the target tissue electrical state. In particular, the ability of the metal oxide coatings of the invention to slough temporarily entrapped serum particles and reestablish the reduction-oxidation potential of the electrode enhance their ability to sense in this manner. The low amplitude sensing characteristics of the electrodes of the invention is attributable in large part to the many-fold increase in surface area creating in effect a larger "antenna." The added surface area increases the spatial extent of the receiving "antenna" enabling it to capture more of the milli- and micro-volt E-fields attributable to myocyte polarizations. In certain instances, the electrodes of the invention will provide increased sensing by 150–600% over that available with a standard IrOx electrode. Sensing of low level signals will become even more critical in natural pacing applications using algorithms designed to detect atrial flutter and fibrillation. Many current electrodes lack the ability to even distinguish atrial from ventricular electrical activity, a difference that the enhanced sensing electrodes of the present invention are capable of detecting.

The implantable stimulation electrodes made by the methods of the invention may also provide the ability to either miniaturize the electrode while retaining the capacity to deliver a suitable charge to the target tissue, or to retain the size of the electrode in the range of the prior art electrodes while gaining the ability to deliver greater energy to the target tissue. In particular, the electrodes of the invention are capable of delivering an adequate pulse to overcome bradycardia or tachycardia with electrodes having an electrically accessible surface area 40% to 80% less than prior art electrodes. However, it should be noted in the case of defibrillation electrodes, those with surface areas which produce current densities greater than about 1.6 to 1.8 amps/cm$^2$ are problematic. Similarly, the electrodes of the invention are also capable of delivering an adequate pulse to overcome tachycardia, which pulse is substantially higher than that of prior art devices, in some cases 40% higher.

The implantable stimulation electrodes made by the methods of the invention are electrodes utilized for a variety of stimulating functions. Because any metal surface of an implantable electrode may be constructed in the manner disclosed herein, the type of implantable electrode is not crucial. Thus, pacing electrodes are suitable for manufacturing via the methods of the invention. Defibrillating electrodes are likewise suitable for manufacturing via the invention.

The methods of the invention comprise removing essentially all of the native metal oxide from a metal surface, which metal surface comprises a valve metal or their alloys in order to create an electrically-accessible area. The inventors have found without the removal of essentially all of the resident oxidation, much of the surface of the electrode will remain of a low conductivity and may become basically non-conductive.

It will be understood by those of skill in the art of manufacturing implantable stimulation electrodes that the order of the treatments described generally above may be altered without departing from the methods of the invention. Thus, one order for treatment entails: (1) removal of the resident metal oxide; (2) macroscopic enhancement; (3) microscopic enhancement; and (4) coating with a different metal oxide. However, it is equally as effective in certain instances to utilize an order for treatment entailing: (1) macroscopic enhancement; (2) microscopic enhancement; (3) removal of the resident metal oxide; and (4) coating with a different metal oxide. In certain instances, macroscopic enhancement will occur before microscopic enhancement. For instance, this would occur where macroscopic enhancement entails corrugating a metal surface and microscopic enhancement entails controlled chemical corrosion. The same can be said between the enhancement procedures and the removal of resident metal oxide treatments. In other instances, it will be best to carry out microscopic enhancement only after macroscopic enhancement.

For instance, good manufacturing procedures would call for first drilling tube-like indentations in the surface prior to treating the surface with acid in a manner to pit the entire surface so that the newly exposed surfaces of the indentations may also be exposed to the acid. The only a priori sequential limitation is that the removal of the resident metal oxides must precede the application of the non-native metal oxide coating. It is also possible, where acid treatment will be used to remove native metal oxide, pit the cleared surface of the electrode, and act as a carrier for the non-native metal oxide, to combine or otherwise integrate the steps in such a manner as to minimize acid loss, in a manner consistent with good chemical manufacturing processes known to those of skill in the art of chemical manufacturing.

An improved method of making a metallic electrode having an valve metal oxide coating for injecting charge into a biological tissue using controlled electrical pulses is also disclosed for an electrode made of a metal and having a metal surface. The improvement consists of removing all native oxides from the metal surface of the electrode, macroscopically and microscopically enhancing its surface area, and applying a coating upon the metal surface of a metal oxide or a mixture of at least two metal oxides selected from the group of metal oxides consisting of oxides of valve metals capable of reversible reduction-oxidation.

DESCRIPTION OF PREFERRED EMBODIMENTS

The following examples are provided to illustrate certain specific best mode methods and devices of the invention but are not meant to be limiting as to the scope of the claimed invention.

Comparing Methods—The methods of the invention provide substantially improved electrodes over those of the prior art. In particular, as will be demonstrated below, these electrodes exhibit improved pacing and sensing functions by virtue of a combination of surface enhancing techniques. The methods employed by the invention can be seen in summary form in Table I below. In similar summary form, Tables II and III show the prior art methods of Baker (U.S. Pat. No. 4,762,136) and Roblee (U.S. Pat. No. 4,677,989), respectively.

By comparison, it can be seen that the prior art methods fail to provide the necessary steps which result in the improved electrodes of the present invention. Specifically, neither of the two prior art methods teach complete removal of the native oxides from the surface of the electrode. Neither do these prior art approaches provide for macroscopic enhancement techniques such as drilling, EDM or indentation. Similarly, neither of these prior art methods teach the advantages of microscopically enhancing the electrode's surface. Finally, even though single oxide coatings are described in each of the prior art methods, neither method provides for mixed oxide coatings as does the present invention. Moreover, neither method combines the surface area enhancement techniques of the present invention with non-native metal oxide coatings.

TABLE I

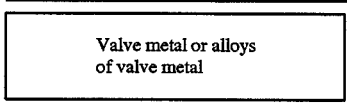
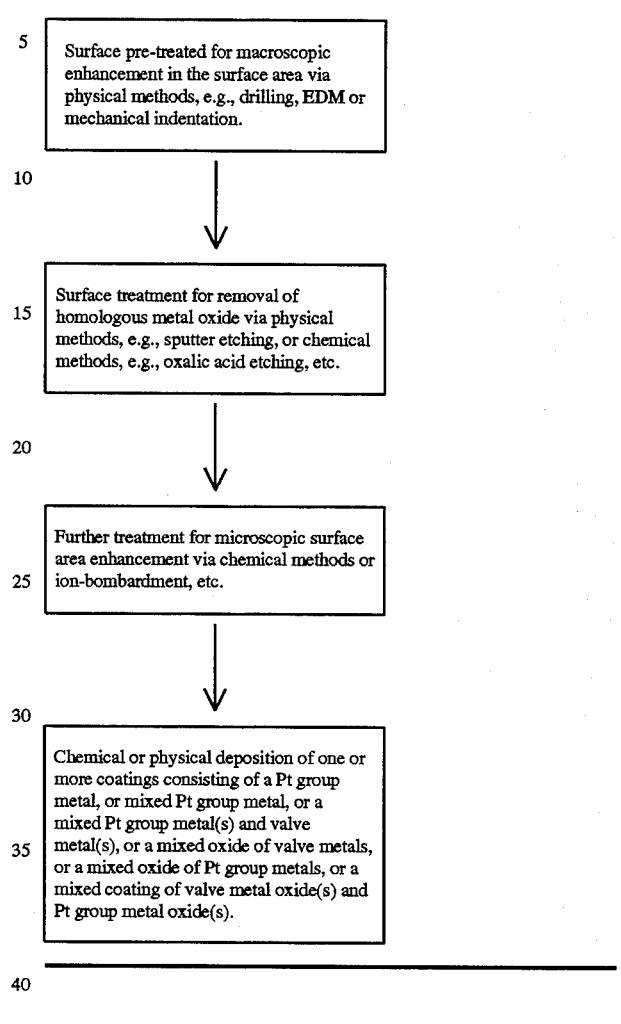

TABLE II

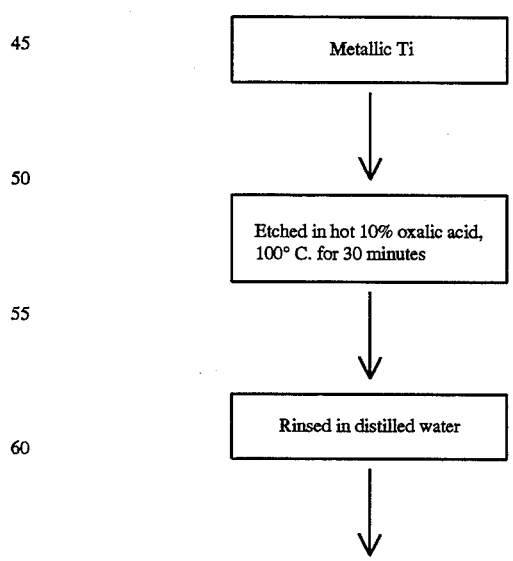

TABLE II-continued

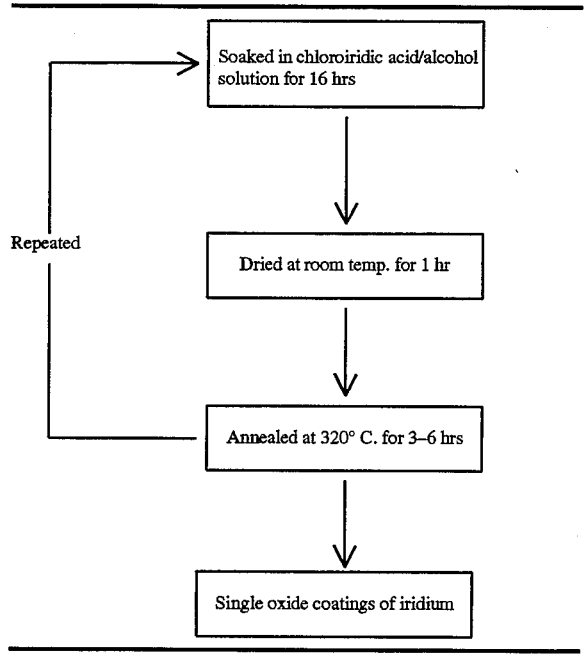

TABLE III

Figure 2:
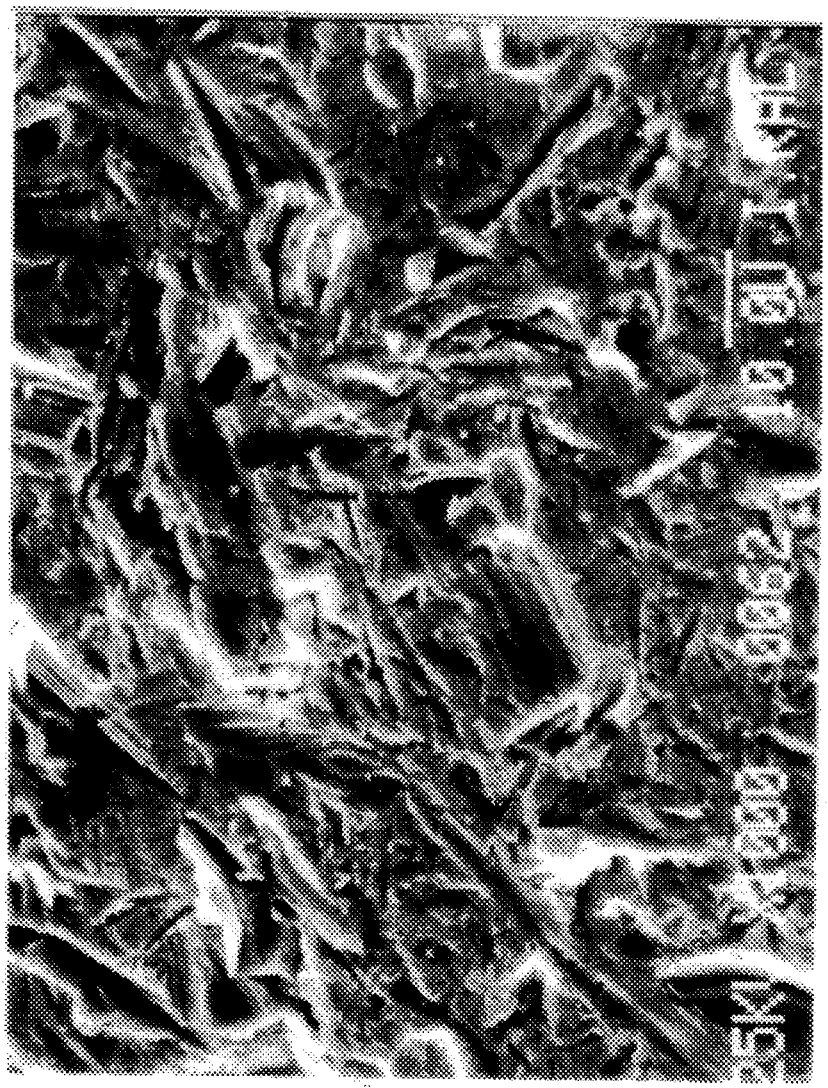
FIG. 2. Titanium tip sandblasted only.

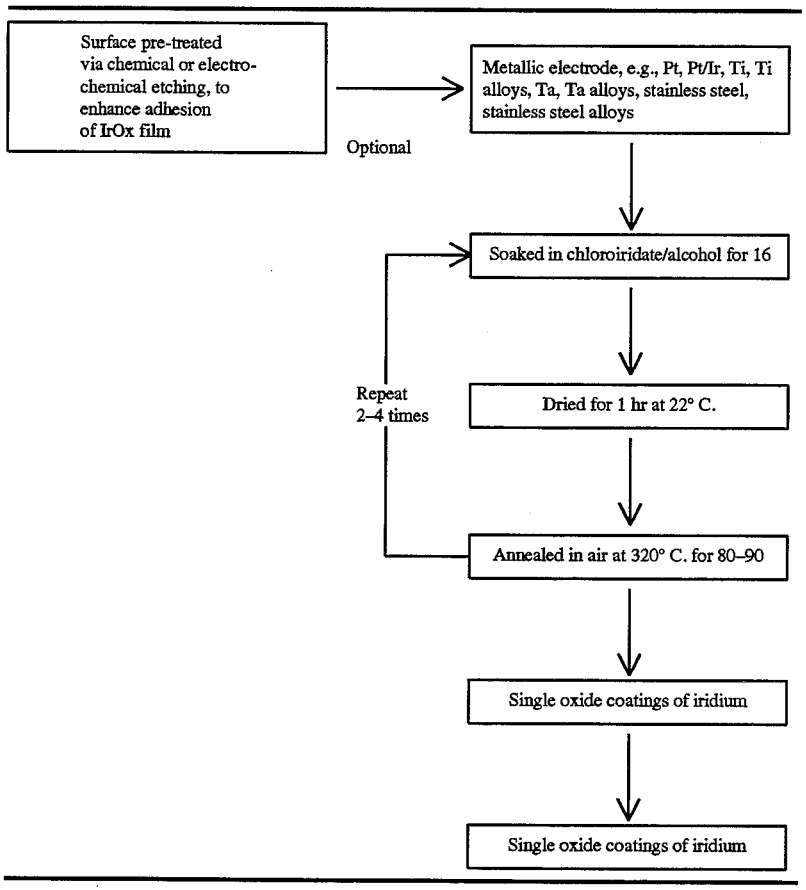

from gross milling manufacturer. Striations resulting from the milling procedure are evident. As discussed in the background section above, one prior art approach is to sandblast such a tip. FIG. 2 shows a titanium tip which has been subjected to sandblasting. Sandblasting increases the surface by a factor of 3–5 over the base substrate, but in the case of titanium, for example, it does not clean all of the native oxide from its surface. In addition, sand gets embedded in the underlying metal in many cases and to a fairly large extent. The sand is usually very fine alumina or silica. These are practically insulators, and so the overall objective of removing a non-conductive native oxide and covering it with an insulator is counterproductive.

Figure 1:
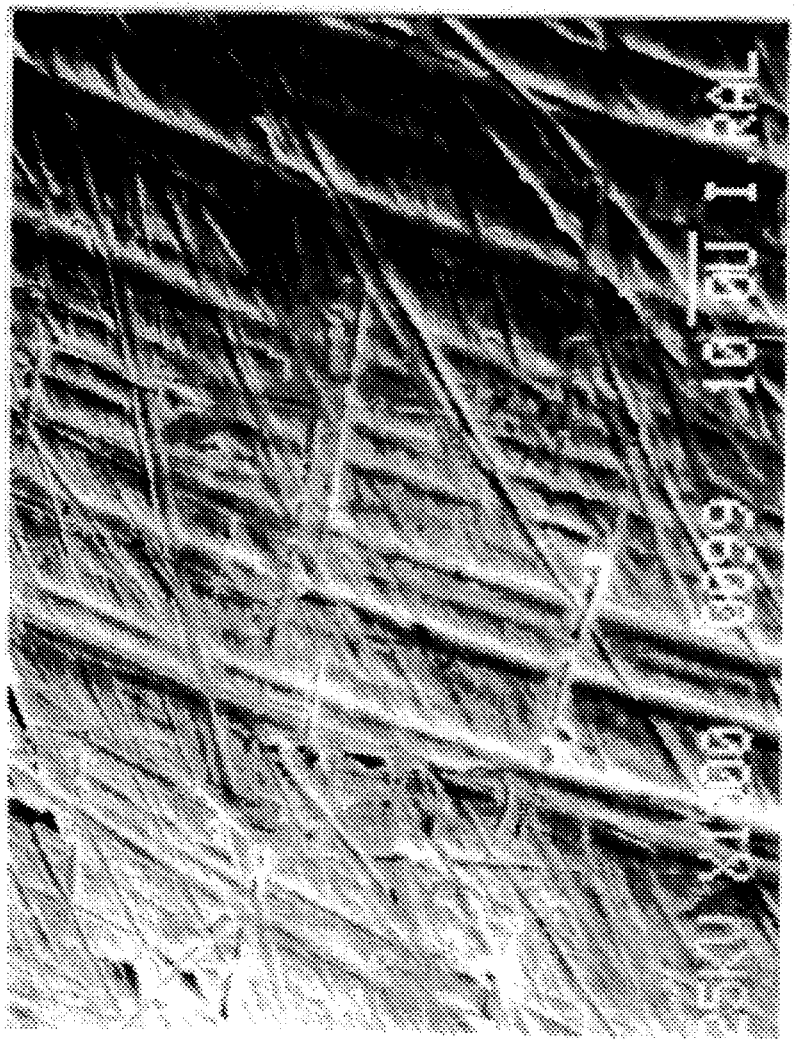
FIG. 1. Base titanium tip as received from manufacturer.
Figure 3:
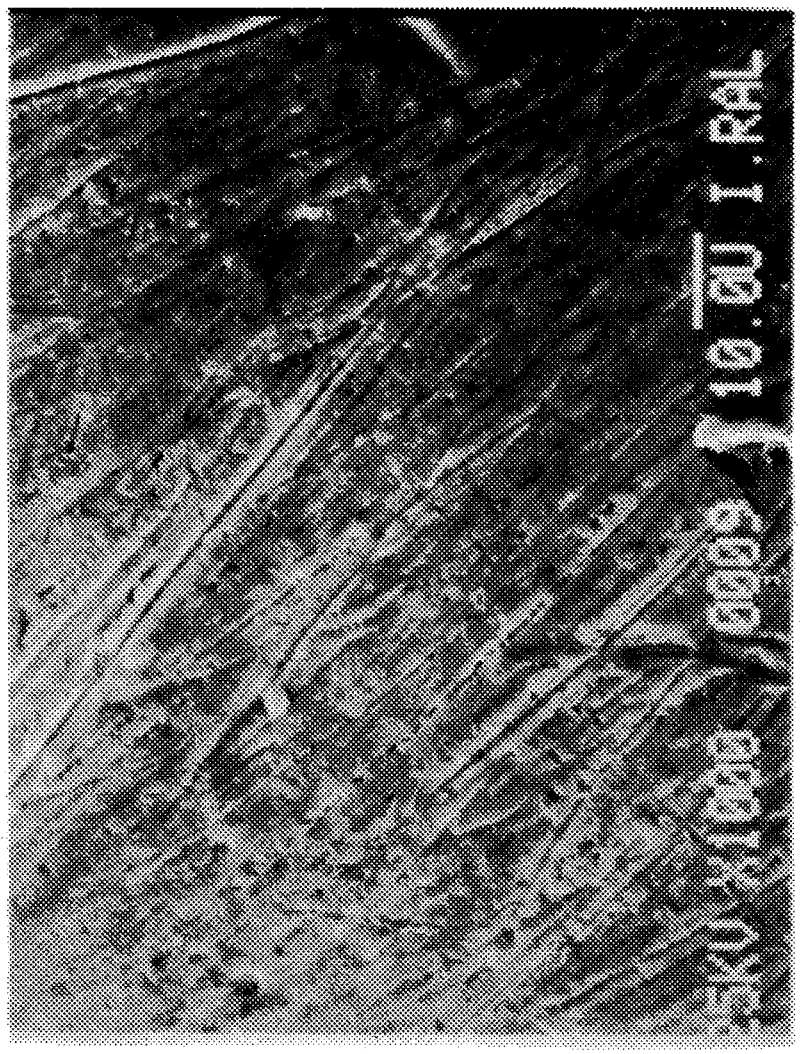
FIG. 3. Base titanium tip "etched" in HCl (1000×).
Figure 4:
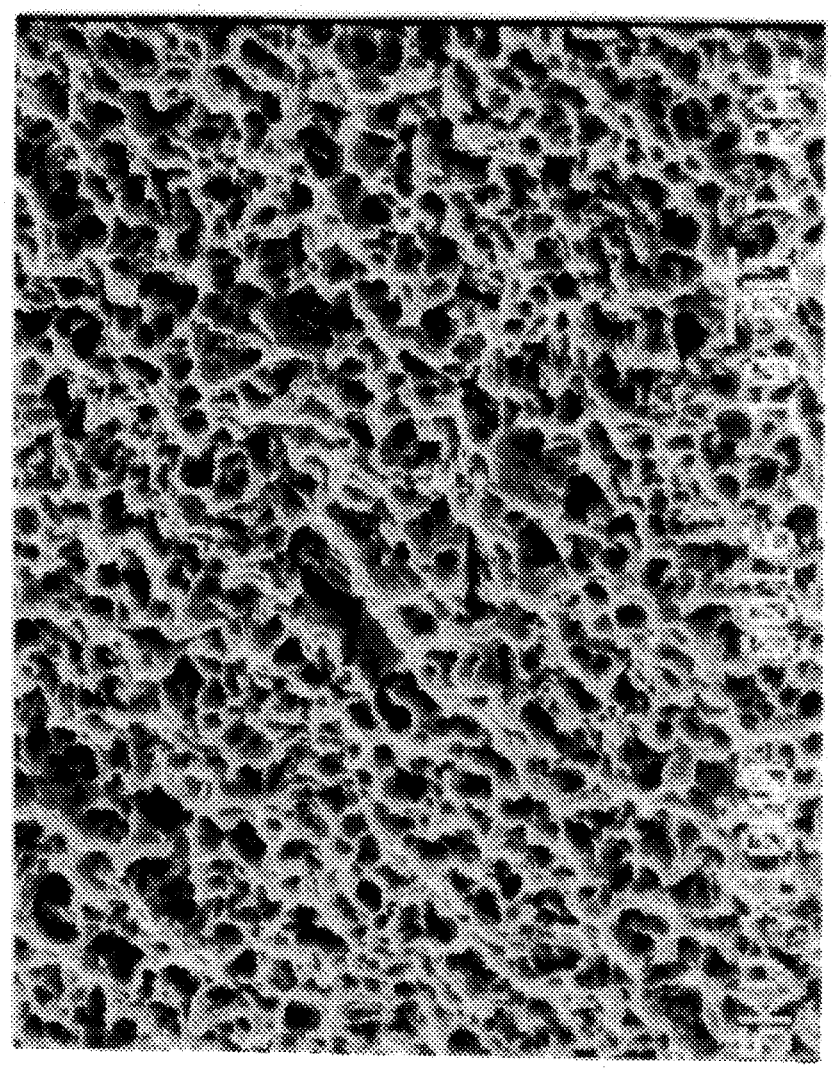
FIG. 4. Titanium tip etched in oxalic acid per invention—no oxide added (1000×).

FIG. 3 depicts a titanium electrode tip which has been treated with HCl (magnification×1000). While there is some smoothing over of the rougher relief aspects of the tip surface shown in FIG. 1, striations are still clearly evident and no pitting is seen. Even with vigorous etching, only surface oxides are removed (and not using HCD. Conversely, as shown in FIG. 4., where a titanium tip is etched in oxalic acid per the teachings of the invention, a highly uniform pitting is seen which lacks the surface striations of FIGS. 1 and 3. Extensive etching with oxalic add begins to dissolve the metal at the grain boundaries. In this instance, no other treatment to enhance surface area was yet accomplished (magnification×1000). The degree of surface enhancement has been estimated to be over 20× that of planar titanium. This enhancement in surface roughness Microenhancing Surface Area—FIG. 1 shows a section of the titanium metal tip portion of the electrode as received reveal an intricate array of regularly pit-shaped interconnected surface projections of about 10 μm in height, spread uniformly across the surface. The montage of the same surface under a low magnification resembles that of a porous sponge. Compared to the sandblasted process (FIG. 1), the oxalic acid etched surface has a much more finer and highly porous texture.

Figure 5:
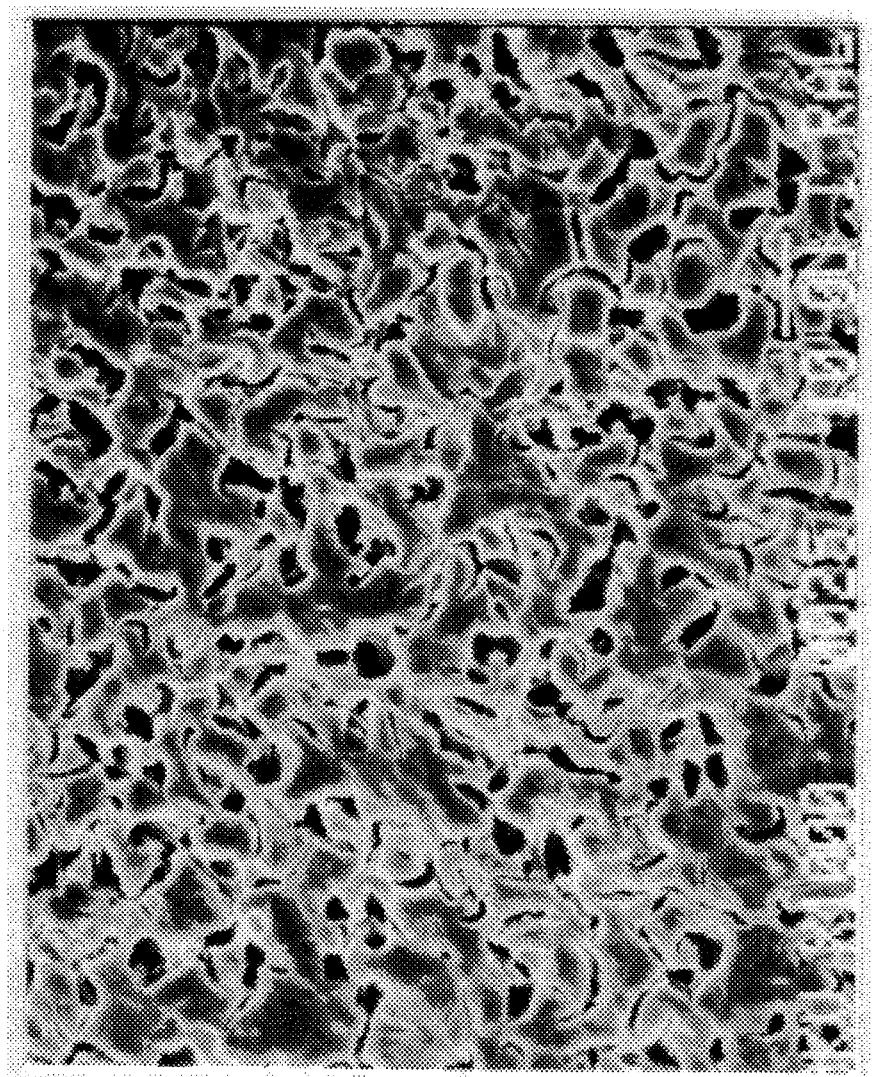
FIG. 5. Ti tip etched in oxalic acid and four coats of iridium oxide applied via method (1000×).
Figure 6:
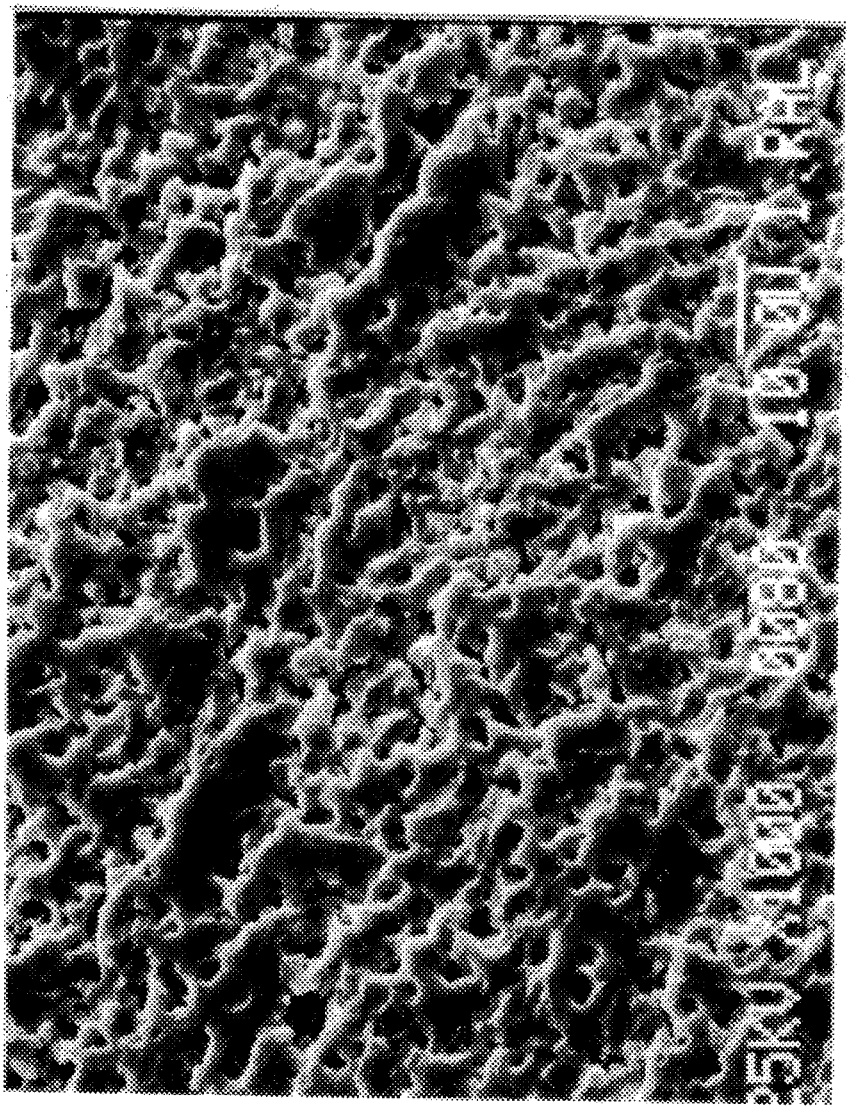
FIG. 6. Ti tip etched in oxalic acid and four coats of ruthenium/iridium oxide applied via method (1000×).

Extending the comparisons to FIG. 5, it can be seen that where a titanium tip is first etched in oxalic add and subsequently coated (four coats) with iridium oxide, the uniform pitting of FIG. 4 is apparently more smooth (magnification×1000). Where the tip is instead treated with a mixed metal oxide, even more of the pit surfaces are filled in. Such a treatment can be seen in FIG. 6 where a titanium tip was first etched in oxalic acid and subsequently subjected to four coats of ruthenium/iridium oxide (magnification× 1000). It should be recalled that this apparent filling in of the pitted surfaces by the coatings of the invention is not a process which causes a blockage of area gained through microscopic enhancement. Rather, the pits are now uniformly filled with the particles of the coating in a manner which substantially increases the surface area even over and above that provided by the pitting itself. Thus, while a smooth, flat surface may be coated with one or a few layers of particles of the coating metals oxides, pits may be filled with many layers of metal oxide by comparison. These many layers of metal oxide provide thereby porosity via channels and intricate "tubules" through and on top of the underlying structure.

The chemical etching process involve the soaking of the soaking of the titanium electrede in a 10% oxalic acid solution at 80° C. This process in the first instance, removes the semiconducting $TiO_2$ from the titanium surface. However, the inventors have found that a substantial improvement in area can be achieved by allowing the acid to contact the electrede surface well beyond that necessary to remove the oxides therefrom. Following the chemical etching procedure, the electrode can then be coated with a corrosion-resistant, stable oxide of either $IrO_2$, $RuO_2$, $SnO_2$, $Ta_2O_5$, or mixtures thereof to protect the underlying metal. The oxide can be deposited either by coating the titanium surface with a liquid precursor such as $IrCl_3$ dissolved in some suitable solvent such as water, isopropanol, or hydrochloric acid, and then decomposing the chloride to the oxide at about 300°–340° C., or it can be deposited as a metal oxide via an evaporative, sputtered, chemical vapor, or jet vapor deposition method, or deposited as a metal and oxidized at high temperatures in an oxygen environment to the oxide. The preferable technique is to use the chloride deposition process.

Figure 8:
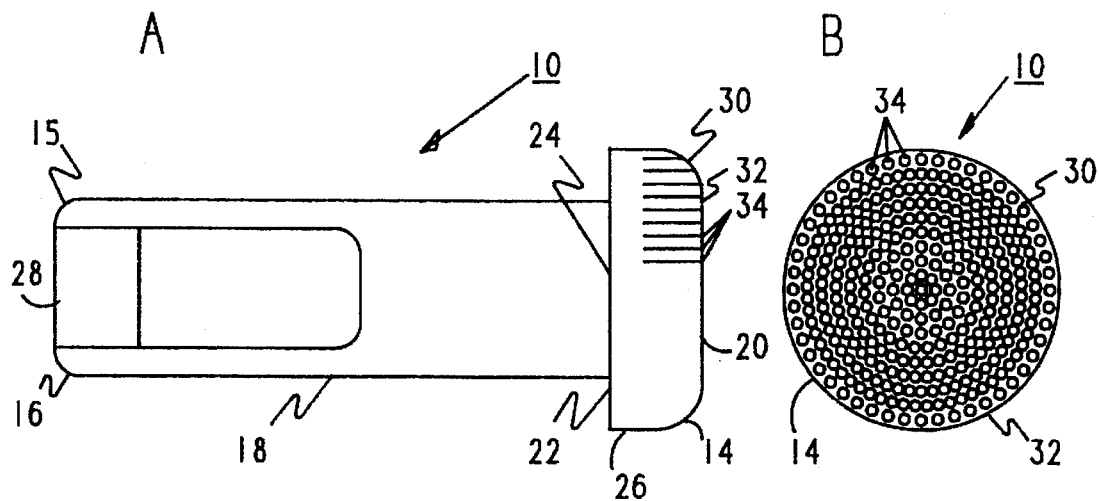
FIG. 8. 8.A—Side cutaway elevation of electrode tip showing bored hole macroscopically enhanced surface; 8.B—End elevation of electrode tip of 8.A.

Macroenhancing Surface Area—FIG. 8 is a side cutaway elevation of an electrode tip showing a bored hole macroscopically enhanced surface. FIG. 8.B is an end elevation of the electrode tip of 8.A. In FIG. 8A and B, an implantable stimulation electrode 10 with a mateable shaft 12 and an endpiece 14 is depicted. At a proximal end 15 of shaft 12 opposite endpiece 14 is an angled surface 16 cut at an angle of 45 degrees relative to the side 18 of shaft 12 and to the proximal end 15. Thereby, endpiece 14 forms on the tip of shaft 12, a button-like electrode tip 26. Beveled surface 30 of electrode tip 26 is an electrically-accessible surface 32 as described above across its entire surface. In order to macroscopically enhance this electrically-accessible surface pursuant to the methods of the invention, a multiplicity of indentations 34 have been drilled into surface 32 at an even spacing distance of approximately on 150 μm and a depth of approximately 100 μm.

In the case of the electrode of FIG. 8, the geometric enhancement over existing electrodes is 3:1. Using this means, it is possible to increase the surface area, say, of a triaxial cut tip of 12 mm² (typical) to 50 mm². This results in an increase of over 4 times the initial surface. When combined with the chemical treatments of the invention as shown above, the surface area of the substrate a/one can be amplified by 40 to 120 times, compared to the triaxial cut bare tip.

EXAMPLE I

A pair of endocardial bipolar bradycardia leads with IrOx coated electrodes were implanted in a dog and the voltage threshold, lead impedance, and sensed R-wave were measured over 16 weeks periodically. One of the electrodes was a commercially available lead of Applicant's company (Intermedics, Inc.), while the electrodes from the second lead were prepared according to one embodiment of this invention, via a rigorous chemical treatment that led to uniform pitting on the titanium electrode surface prior to coating with IrOx.

Figure 9:
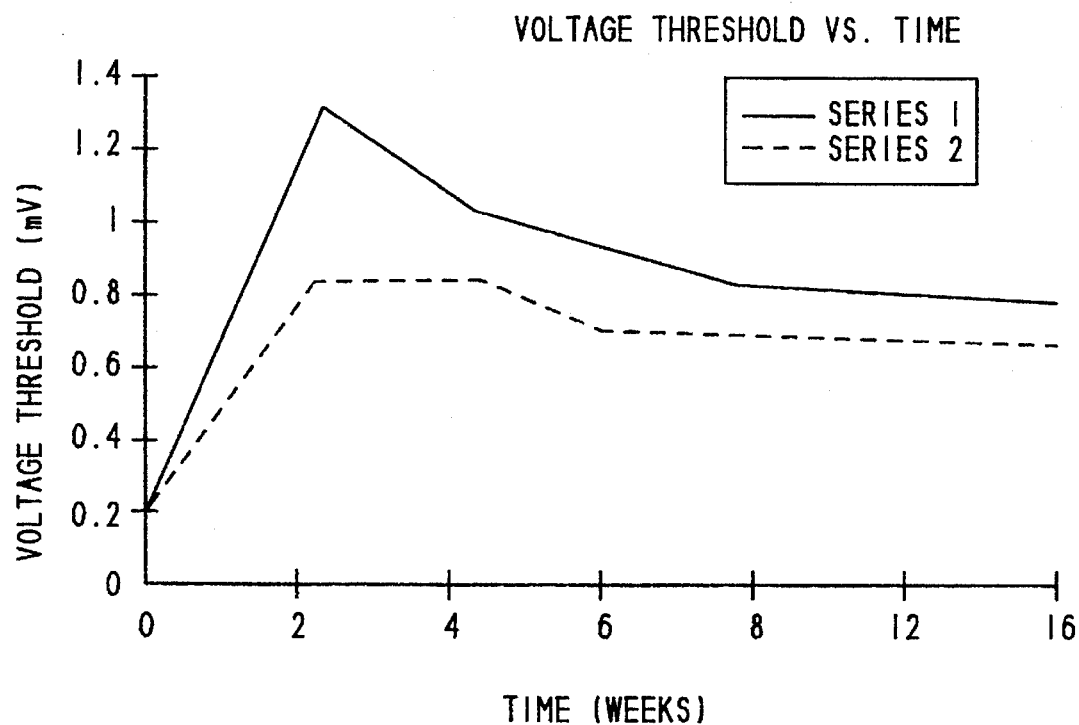
FIG. 9. Test of voltage threshold versus time on two $IrO_x$ coated leads—series 1 lead prepared using known techniques, series 2 lead prepared using the methods of the invention.

FIG. 9 shows the results of the test as it relates to voltage threshold versus time on the two IrOx coated leads. The voltage threshold remained lower for the electrode of the invention throughout the experimental period. This included a substantially lower acute threshold as well as a somewhat lower chronic threshold.

Figure 10:
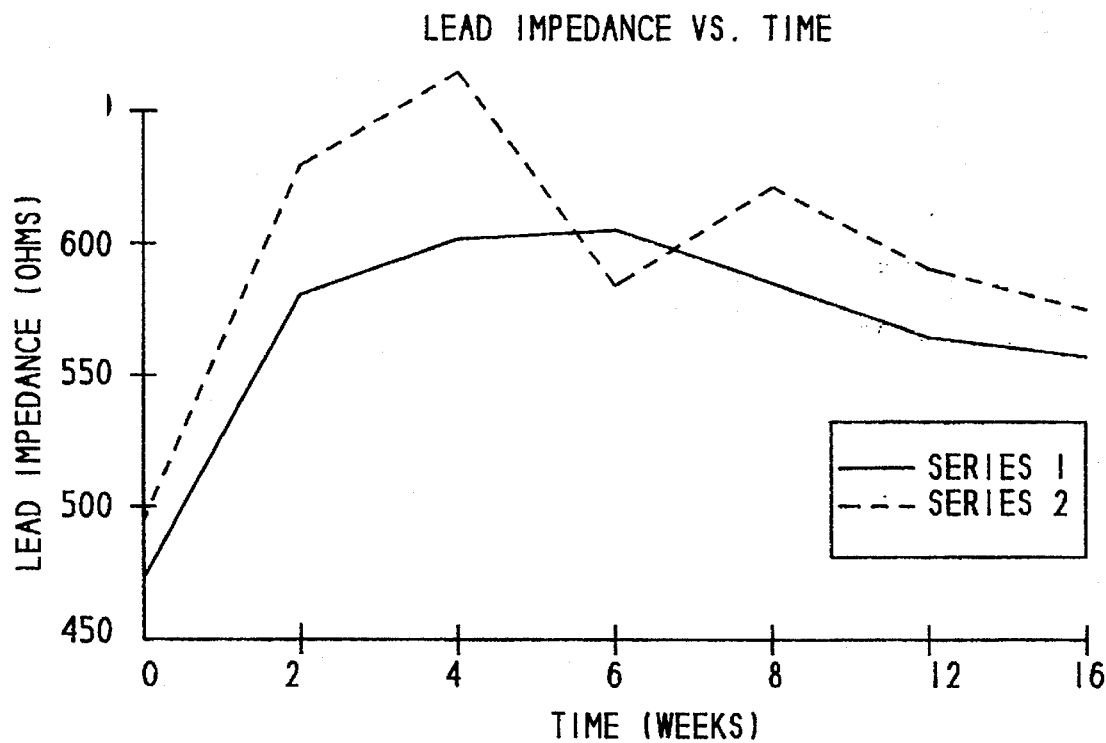
FIG. 10. Test of lead impedance versus time on two $IrO_x$ coated leads—series 1 lead prepared using known techniques, series 2 lead prepared using the methods of the invention.

FIG. 10 shows the results of the test as they relate to lead impedance versus time on the two IrOx coated leads. The lead impedance is higher for the electrode of the invention throughout most of the test period. There was an unexplained dip in the lead impedance of the lead of the invention around the 6th week.

Figure 11:
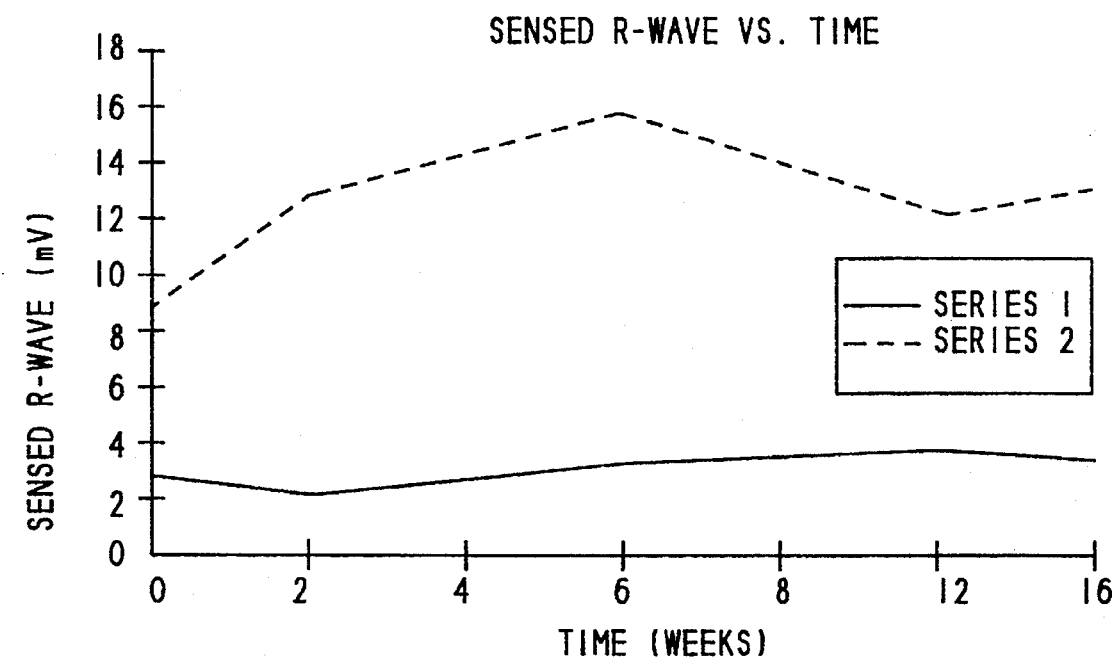
FIG. 11. Test of sensed R-wave versus time on two $IrO_x$ coated leads—series 1 lead prepared using known techniques, series 2 lead prepared using the methods of the invention.

FIG. 11 shows the results of the test as they relate to the sensed R-wave versus time on the two IrOx coated leads. In this case there is an over 300% improvement in the sensing threshold of the leads of the invention over the control lead.

EXAMPLE II

Animal studies were performed using the prepared and virgin electrodes in a directly comparative and statistically designed experiment. The experiment was structured to show the differences in energy transfer between virgin metal electrodes and those valve metals prepared and coated according to the invention. In this instance, the energy measured was defibrillation threshold (DFT), or the minimum joules required to cardiovert a fibrillating heart.

Electrode Preparation

Defibrillation leads were prepared in the following manner: A total of four electrodes were assembled; two with active electrode lengths of 1", and two with length of 2". One electrode of each different length was coated and prepared according to the invention; the remaining two were left as virgin titanium. All four electrodes were then fabricated into custom defibrillation leads for animal testing, each identical in construction and manufacture.

Test Protocol

Defibrillation pulses were delivered via a commercially available Automatic Cardiac Defibrillator (ACD), which delivered Schuder's truncated exponential pulse (STEP) at 6.5 mS in the first phase, and 3.5 mS in the second. The energy delivered (in joules) was varied by altering the voltage according to $E=\frac{1}{2}C(V_1^2-V_2^2)$. with $V_1$ the voltage at the beginning of the pulse, $V_2$ the voltage at the pulse truncation point, and C a constant at $175*10^{-6}$ farads.

Additional devices used were a "patch" electrode, approximately 32 cm³, consisting of titanium wire mesh of wire 0.004" diameter embedded in silicone substrate, and a titanium can of approximately 107 cm² in surface area. The design matrix varied electrode type (either virgin titanium or prepared and coated), electrode polarity, electrode location, and electrode fixation in the right ventricle. A total of 12 data points were tabulated; six to test the influence of the coated electrodes, and six to investigate the effect of the virgin titanium on defibrillation thresholds (DFT's). The test conditions/configurations were:

1,2,2—1" electrode in animal right ventricle (RV), 2" electrode in the superior vena cava (SVC), polarity such that the electrode in the RV was anodic during the first part of STEP, and RV electrode unfixed in the heart.

3,2,2—1" electrode in animal right ventricle (RV), the titanium "patch" electrode in the lateral chest wall, polarity such that the electrode in the RV was anodic during the first part of STEP, and the RV electrode unfixed in the heart.

3,1,1—1" electrode in animal right ventricle (RV), the titanium "patch" electrode in the lateral chest wall, polarity such that the electrode in the RV was cathodic during the first part of STEP, and the RV electrode affixed to the endocardial septum.

2,1,2—1" electrode in animal right ventricle (RV), 2" electrode in the RA, polarity such that the electrode in the RV was cathodic during the first part of STEP, and the RV electrode unfixed in the heart.

1,1,1—1" electrode in animal right ventricle (RV), 2" electrode in the superior in the superior vena cava (SVC), polarity such that the electrode in the RV was cathodic during the first part of the STEP, and the RV electrode affixed to the endocardial septum.

4,1,2—1" electrode in animal right ventricle (RV), titanium can electrode implanted subcutaneously in lateral chest wall, polarity such that the electrode in the RV was cathodic during the first part of STEP, and the RV electrode unfixed in the heart.

Results

The defibrillation threshold in joules obtained for both coated and virgin electrode surfaces was measured. It was found that the prepared and coated electrode surfaces, in any configuration, consistently had a lower energy requirement to successfully defibrillate the heart. The lowest energy requirement was satisfied by condition 4,1,2 using a prepared and coated electrode in the RV.

EXAMPLE III

As before, two sets of defibrillation electrodes were prepared and virgin, in 2" active lengths. Pulses to the electrodes were delivered by a custom build monophasic generator, which delivered 700 Vdc peak pulses at 10 mS duration. The energy delivered to the system was constant, determined by the fixed capacitance (C=175·10⁻⁶ farads) of the pulsing mechanism. The cell electrolyte consisted of a Lactated Ringers/deionized H₂O solution, 50/50 % v, at a temperature of 22° C., which resulted in a bulk impedance between the electrodes, measured at 10 KHz, of approximately 50 ohms. Voltages were measured by a high input impedance voltmeter which measured the potential difference between the chosen electrode and a Ag/AgCl reference electrode, while current measurements were obtained by a clamp-on probe on one of the electrode cables. Data was collected by computer as presented at 3, 150 and 300 total pulses to ascertain the degree of deterioration and/or efficiency of the electrode behavior over time. The electrode system was pulsed 300 times in succession, at an interval of 120 seconds between pulse events. For purposes of this experiment, the two prepared electrodes were arbitrarily given serial numbers 241 and 252, while the virgin items were assigned numbers 238 and 246.

It was shown that the "available" voltage at the control electrode drops dramatically between 3 and 150 total shocks, and even more between 150 and 300 shocks. The total $\Delta V$ between pulse 3 and 300 was measured at approximately −40 volts, which corresponds to a loss of efficiency and available energy. Where prepared and coated electrodes were used according to the invention, the $\Delta V$ of the electrode between 0 and 300 pulses is minimal, indicating that the electrode of the invention is reliable and stable.

The measured current between the anodic and cathodic control titanium electrodes with respect to ground was measured. Of particular interest here was the current produced by the titanium electrodes at the beginning of the pulse. It was seen that the level of current varied from a low of 14A, to a high of 18A. The measured current of the electrodes of the invention, was measured at intervals of 3, 150, and 300 pulse deliveries. It was evident that the current deviation was minimal (approximately 3 amps) over the pulsing episode; also, the initial and final levels of current, under the same conditions, were considerably higher than those in the titanium case.

In the case of virgin titanium, the voltage generated at the anodic electrode surface declined as a function of the number of pulses. In the case of the prepared and coated electrodes, however, the voltage level remained constant over the 300 pulses given. This may be attributed to native oxides of the form TiOx forming on the unprepared electrode surface, while the altered, high-surface-area electrode remains relatively "clean." These examples show the stability of the treated electrode surface over sustained use. A more dramatic comparison can be ascertained by comparing the active currents produced by the virgin material, with those promulgated by the treated electrodes.

In a capacitive system which discharges into a simple impedance, as in the case here, the energy E delivered across the resistance is given by definition as $E=v(t)\cdot i(t) \cdot t$, or power·time. In the equation, $v(t)$ is the voltage as a function of time in joules/coulomb, $i(t)$ a representation of current in amps or coulombs/second, and t the pulse duration in seconds. In this case, the factors of E may be written as: $v(t)=[i(t)\cdot R]$, $i(t)=[i_o e^{(2t/RC)}]$, with R a constant impedance. Thus, the total energy (in joules) delivered to the resistive load is given by $E=[i_o e^{(-2t/RC)}]\cdot [t]$, or, combining terms:

$$E = i_o^2 \cdot R \cdot t \cdot e^{(-2t/RC)}$$

This shows the total energy delivered to the load is proportional to the square of the applied current and in addition, this current is modified by a strong exponential term which dictates that most of the energy is delivered at the beginning of the pulse (@t≧0).

The prepared and treated electrodes of the invention have a higher initial current, >66% more, when compared with the virgin metal. This higher initial current may be due to the higher surface area of the prepared electrode, resulting in a lessened current density at the electrode/electrolyte interface. The rise in current over the pulse episode is probably due to the formation of complex chemical species formed by synthesis and breakdown in the electrolyte, attributed to the intense E-field during the pulse. In any case, the current rise is limited in the prepared and treated electrode, indicating a more stable and reliable system.

EXAMPLE IV

The following electrodes were used for comparative testing: (1) Titanium coated with Pt/IX alloy; CPI Serial #0072-002577; (2) Pt/Ix alloy only; Medtronic Serial #TAL001884K; and (3) IrOx coated titanium, prepared according to invention.

The experimental cell for all tests consisted of the lead under test as the working electrode (w.e.), a standard calomel reference electrode in close proximity to the w.e., and a solid titanium rod as the counter electrode (c.e.). The aqueous electrolyte was a miscible solution of 1:2 Ringers lactate and deionized $H_2O$, which gave a bulk impedance of ≈50 Ω at 10 kH between w.e. and c.e. Cyclic voltammetry was performed on each lead at 1 volt with respect to $V_{ref}$ at a scan speed of 5 mV/sec. The double-layer capacitance reported was computed from the data as: $C_{dl}=i/\delta V/\delta t$ is the scan speed, and $C_{dl}$ is in units of farads. The charge injection fraction reported was obtained from the integral of $C_{dl}=\int idt$, where the limits were taken between 0 and 1 volt on the voltammogram, and $C_{dl}$ is in coulombs.

The interface (lead/connective tissue capsule) showed minimal reactivity. The capsule varied in thickness from 0.25 to 1.25 mm. It was composed primarily of dense fibrous connective tissue with focal areas of increased cellularity and focal dystrophic mineralization. Areas of increased cellularity were along the medial wall of the lead tip (2.0 mm) and the distal aspect. These areas were composed of an admixture of homogeneous, eosinophilic material (blood proteins), macrophages, scattered neutrophils, and spindle-shaped cells (fibroblasts).

This represented an early stage of transition to fibrous connective tissue. The adjacent myocardium showed isolated myocytes within collagen substrate and accentuation of interstitium. Most of the isolated myocytes showed some degree of attenuation. These changes extended approximately 0.25 mm into the myocardium. Additionally, mild, multifocal aggregates of adipose cells extended throughout the myocardium. The epicardium was within normal limits. Electrode substrate tips for bradycardia electrodes described in prior arts are either spherical, or have biaxial (criss-cross) or triaxial cuts on the spherical surface.

The present invention has been described in terms of particular embodiments found or proposed to comprise preferred modes for the practice of the invention. It will be appreciated by those of skill in the art that, in light of the

| LEAD MATERIAL CHARACTERIZATION STUDY | | |
|---|---|---|
| ELECTRODE MATERIAL | DOUBLE LAYER CAPACITANCE | CHARGE INJECTION FRACTION (Between 0 and +1 Volts) |
| Coated Ti, lead prepared via method (macro and micro surface enhancement) | $3000 \times 10^{-3}$ farads | $102.6 \times 10^{-3}$ coulombs |
| Pt—Ir alloy only | $20 \times 10^{-3}$ farads | $20.89 \times 10^{-3}$ coulombs |
| Ti, coated with Pt | $4 \times 10^{-3}$ farads | $6.987 \times 10^{-3}$ coulombs |

EXAMPLE VI

Figure 7:
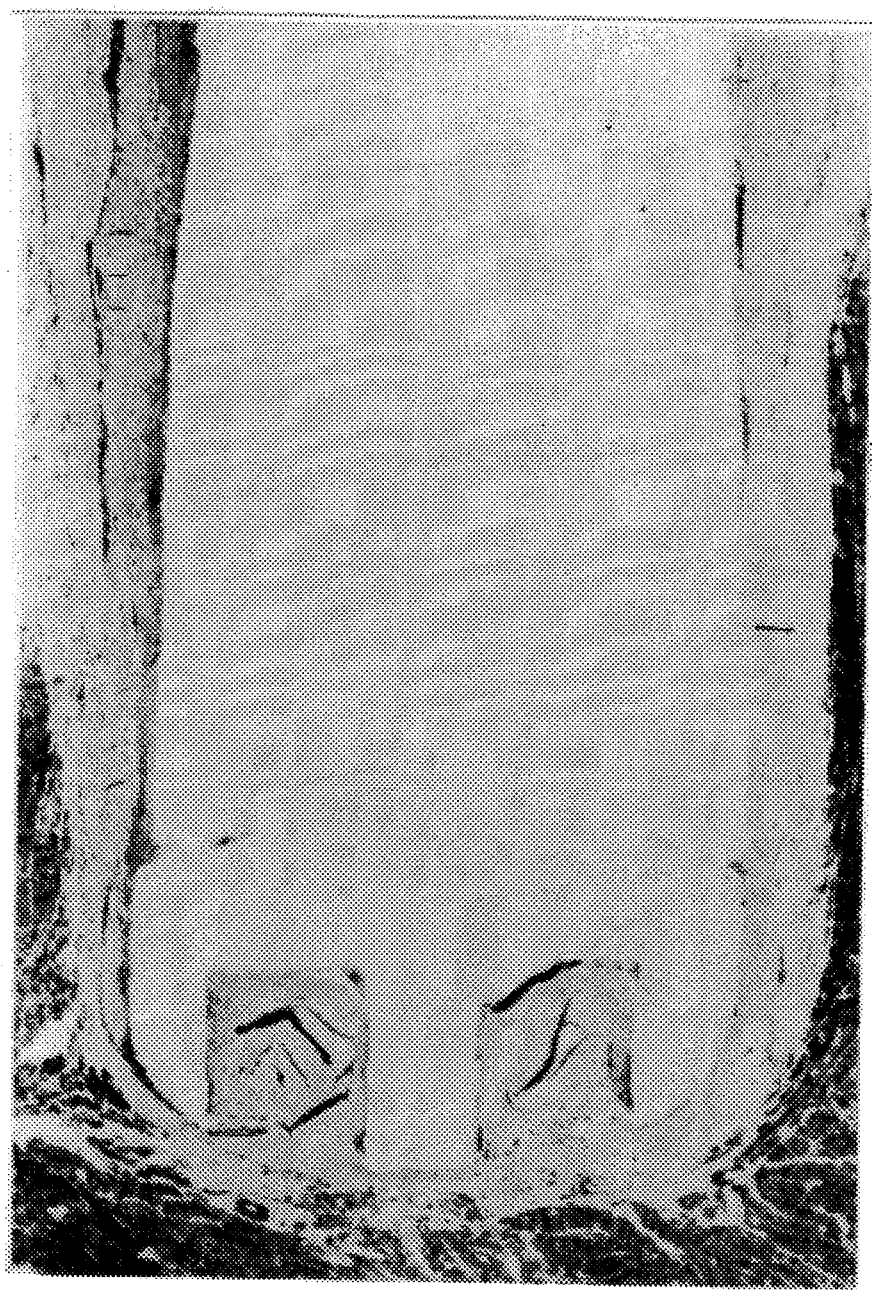
FIG. 7. Photomicrograph of crossection of lead of invention/connective tissue interface twelve (12) weeks post-implantation (hematoxylin and eosin stained section, 5 micrometers, magnification×100).

Leads which had been implanted in dogs were explanted and sectioned. FIG. 7 shows a photomicrograph of a cross-section of a lead of invention and the connective tissue interface twelve (12) weeks post-implantation (as stained with hematoxylin and eosin, section 5 micrometers, magnification×100). The minimal reactivity is characterized by healthy canine myocytes and modest encapsulation. The electrode tip was IrOx coated after oxalic acid treatment. After a few weeks in the apex of the heart, the electrode tip becomes "fixed" to the myocardium, and develops a fibrous capsule around the tip of the electrode typically in the range 0.7 to 1.0 mm thickness. Post-mortem examination of the electrodes indicated that the standard electrode (prior art) developed more fibrous connective tissue around the lead tip and was deemed to be less stable, whereas the lead tip processed from this invention developed less fibrous connective tissue and hence demonstrated greater stability. In addition, the fixation was significantly improved over prior art electrode with no blood getting into the lead tip (a beneficial effect). The thickness of the fibrous capsule was only 0.25 mm. In all respects, the electrode from this invention behaved remarkably superior to an electrode from prior art, with the same surface coating.

More specifically, it was concluded that the transmural section of myocardial tissue was characterized by a fibrous connective tissue capsule partially attached to the endocardium and focally extending into the myocardium (FIG. 7).

present disclosure, numerous modifications and changes can be made in the particular embodiments exemplified without departing from the intended scope of the invention. For example, by virtue of the ability of the electrodes of the present invention to be miniaturized and by virtue of the increased sensing abilities of these electrodes, such electrodes may find usefulness in intercranial neural stimulation and other neural stimulation applications. Similarly, other excitable tissues including muscle (skeletal, smooth, as well as cardiac), and nervous tissue (spinal, retinal, brain) may be stimulated with the electrodes of the invention. All such modifications are intended to be included within the scope of the appended claims.

What is claimed is:

1. A method of manufacturing an implantable stimulation electrode, comprising:

removing substantially all native metal oxide from a metal surface further comprising a metal selected from the group consisting of valve metals or their alloys in order to create an electrically-accessible area;

enhancing said electrically-accessible area to create a first enhanced surface area;

further enhancing said first enhanced surface area to create a second enhanced surface area, wherein said second enhanced surface area has greater electrically-accessible surface area than does said first enhanced surface and, applying lastly a non-native coating upon said second enhanced surface area comprising a mixture of at least three metal oxides selected from the group consisting of oxides of ruthenium, iridium, titanium, and tantalum.

2. The method of claim 1, wherein said electrode comprises a pacing electrode.

3. The method of claim 1, wherein said electrode comprises a defibrillating electrode.

4. The method of claim 1, wherein said first enhanced area comprises an area which is indented.

5. The method of claim 4, wherein said area which is indented comprises a multiplicity of tube-shaped receptacles.

6. The method of claim 5, wherein said receptacles are between about 10 and 90% of the depth of said metal surface.

7. The method of claim 5, wherein said receptacles are between about 20 and 100 micrometers in diameter.

8. The method of claim 5, wherein said receptacles are between about 20 and 30 micrometers in diameter.

9. The method of claim 5, wherein said receptacles occur at a density of at least 150 to 350 receptacles per square millimeter of said metal surface.

10. The method of claim 1, wherein said first enhanced area comprises an area which is corrugated.

11. The method of claim 10, wherein said area which is corrugated increases the electrically-accessible area by a factor of at least 85% as compared to an implantable stimulation electrode lacking said first and second enhanced surface areas.

12. The method of claim 1, wherein said second enhanced area comprises an area which is chemically corroded.

13. The method of claim 12, where said area which is chemically corroded is corroded by exposure to an acid.

14. The method of claim 13, wherein said acid is oxalic acid.

15. The method of claim 13, wherein said exposure to said acid induces a density of pitting of at least 50,000 to 110,000 pits per square millimeter.

16. The method of claim 13, wherein said exposure to said acid results in a uniformity in the electrically-accessible surface.

17. The method of claim 1, wherein said second enhanced area comprises an area which is bombarded with ions.

18. The method of claim 1 wherein said mixture comprises ruthenium oxide, iridium oxide, and tantalum oxide formulated at a ratio of 50:25:25 weight percent, restrictively.

19. A method of making a metallic electrode having an valve metal oxide coating for injecting charge into a biological tissue using controlled electrical pulses, said electrode made of a metal and having a metal surface, wherein the improvement consists of non-native metal oxide coating upon said metal surface a mixture of at least three metal oxides selected from the group consisting of oxides of ruthenium, iridium, titanium, and tantalum.

20. A method of manufacture an implantable stimulation electrode, comprising:

removing substantially all native metal oxide from a metal surface further comprising a metal selected from the group of metals consisting of valve metals or their alloys in order to create an electrically-accessible area;

preventing formation of native metal oxide upon said metal surface; and, applying a non-native coating upon said metal surface comprising a metal oxide or a mixture of at least two metal oxides selected from the group of metal oxides consisting of oxides of ruthenium, iridium, titanium, and tantalum.

* * * * *